(12) United States Patent
Kuroda et al.

(10) Patent No.: US 8,283,443 B2
(45) Date of Patent: Oct. 9, 2012

(54) METHOD FOR PURIFYING PROTEIN

(75) Inventors: Akio Kuroda, Higashihiroshima (JP); Takeshi Ikeda, Higashihiroshima (JP)

(73) Assignee: Hiroshima University, Higashihiroshima-shi (JP)

( * ) Notice: Subject to any disclaimer, the term of this patent is extended or adjusted under 35 U.S.C. 154(b) by 477 days.

(21) Appl. No.: 12/500,526

(22) Filed: Jul. 9, 2009

(65) Prior Publication Data
US 2010/0029905 A1    Feb. 4, 2010

(30) Foreign Application Priority Data
Jul. 31, 2008   (JP) ................................ 2008-198819

(51) Int. Cl.
*C07K 1/22* (2006.01)
(52) U.S. Cl. ........................ 530/344; 435/69.7; 530/413
(58) Field of Classification Search ........................ None
See application file for complete search history.

(56) References Cited

U.S. PATENT DOCUMENTS
2009/0118142 A1    5/2009  Kuroda et al.

FOREIGN PATENT DOCUMENTS
WO    WO-2007/055288 A1    5/2007

OTHER PUBLICATIONS

Schauer-Vukasinovic et al. Purification method for recombinant proteins based on a fusion . . . Analytical and Bioanalytical Chemistry. Jun. 29, 2002, vol. 373, pp. 501-507.*
Varady et al. Rapid High-Performance Affinity Chromatography on Micropellicular Sorbents. Journal of Chromatography. 1988, vol. 458, pp. 207-215.*
Fuchs, S.M. and Raines, R.T. (2005). "Polyargenine as a multifunctional fusion tag," *Protein Science* 14:1538-1544.
Taniguchi, K. et al. (2007). "The Si-tag for immobilizing proteins on a silica surface," *Biotechnology and Bioengineering* 96:1023-1029.

* cited by examiner

*Primary Examiner* — Jeffrey E Russel
(74) *Attorney, Agent, or Firm* — Morrison & Foerster, LLP

(57) ABSTRACT

The present invention provides a method for purifying a protein, includes the step of: contacting a fusion protein of a first protein and a second protein with a bivalent cation-containing solution, the fusion protein being adsorbed to a silicon oxide-containing substance, the first protein being capable of binding to the silicon oxide-containing substance in a solution containing 0.1M sodium chloride. With this arrangement, it is possible to easily produce large quantity of proteins which are high in purity without sacrificing activity of the proteins.

9 Claims, 4 Drawing Sheets

METHOD FOR PURIFYING PROTEIN

This Nonprovisional application claims priority under 35 U.S.C. §119(a) on Patent Application No. 2008-198819 filed in Japan on Jul. 31, 2008, the entire contents of which are hereby incorporated by reference.

TECHNICAL FIELD

The present invention relates to a method for purifying a protein. More specifically, the present invention relates to an affinity purification method using molecules which can be adsorbed to a silicon oxide-containing substance.

BACKGROUND ART

A protein is one of main substances constituting an organism, and has been widely used as a medical product, a medical material or the like. Conventionally, a protein to be used has been obtained by various methods (e.g. purification of a protein from a natural material). In recent years, a method for forcibly expressing a target protein in various kinds of cells has been used, and such protein has been used in various ways. However, such a conventional method undesirably requires complicated steps to purify a desired protein from a cell. Further, a great amount of protein is required in some applications. However, such a classical method unfortunately cannot produce a large amount of protein.

Various methods have been developed which allow easy purification of proteins which are forcibly expressed in various kinds of cells. Examples of such methods include a method in which a fusion protein having a tag of various kinds attached thereto are forcibly expressed in various kinds of cells, respectively, and then the fusion proteins are purified by adsorption between the tag and a carrier having affinity with the tag. Until now, various kinds of tags have been developed. Examples of such tags include a GST protein, an HA tag, a Flag tag, a Myc tag, and a His tag.

Citation List
  Patent Literature 1
  WO2007/055288 Pamphlet (Publication Date: May 18, 2007)
  Non-Patent Literature 1
  Taniguchi, K. et al., The Si-tag for immobilizing proteins on a silica surface. Biotechnol. Bioeng. 96: 1023-1029 (2007)
  Non-Patent Literature 2
  Fuchs, S. M. and Raines, R. T. Polyarginine as a multifunctional fusion tag. Protein. Sci. 14: 1538-1544 (2005)

Currently, functional analysis of various kinds of proteins is in progress, and such tags are used in examining interaction between plural proteins. Since the analysis needs to be conducted from many different perspectives, wider variety of tags used for protein purification are better.

SUMMARY OF INVENTION

The present invention was attained in view of the above problems, and an object of the present invention is to find tags available for protein purification and to provide a novel method for purifying a protein.

The inventors of the present invention have studied on a technique for causing proteins to be adsorbed onto a surface of a silicon oxide-based board, and have found that there exist proteins each of which specifically binds to a silicon oxide-containing substance (see Patent Literature 1 and Non-Patent Literature 1, for example). Further, it is reported that a protein having nine arginine residues (polyarginine tags) attached thereto can be directly adsorbed to a surface of glass or a silica resin without losing an enzymatic activity thereof (see Non-Patent Literature 2, for example). These techniques have an advantage of capable of causing a protein to be tightly adsorbed onto a board. However, these techniques require use of strong acid or strong base in order to dissociate the protein from the silicon oxide-containing substance so that the board can be reused. The protein thus dissociated could not be reused. This means that these techniques cannot be used as a protein collecting technique.

Based on a unique viewpoint, the inventors of the present invention has examined whether a protein which is adsorbed to a silicon oxide-containing substance can be dissociated from the silicon oxide-containing substance with the use of a cation solution or an anion solution. However, even a NaCl solution, which is often used in column chromatography, having the highest concentration could not dissociate a protein from a silicon oxide-containing substance to which the protein is adsorbed. However, as a result of diligent studies based on their unique viewpoint, the inventors of the present invention found that a protein adsorbed to a silicon oxide-containing substance can be dissociated from the silicon oxide-containing substance with the use of a bivalent cation-containing solution. Based on this finding, the present invention was attained.

A method for purifying a protein of the present invention, includes the step of: contacting a fusion protein of a first protein and a second protein with a bivalent cation-containing solution, the fusion protein being adsorbed to a silicon oxide-containing substance, the first protein being capable of binding to the silicon oxide-containing substance in a solution containing 0.1M sodium chloride.

It is preferable that the method for purifying a protein of the present invention, further includes the step of: adsorbing the fusion protein to the silicon oxide-containing substance.

It is preferable that the method for purifying a protein of the present invention, further includes the step of: expressing the fusion protein in a transformant.

It is preferable that the method for purifying a protein of the present invention, further includes the step of: causing second DNA encoding the second protein to be linked in-frame with first DNA encoding the first protein.

In the method for purifying a protein of the present invention, it is preferable that the bivalent cation-containing solution is a $MgCl_2$ solution, a $CaCl_2$ solution or a $NiCl_2$ solution.

In the method for purifying a protein of the present invention, it is preferable that the bivalent cation-containing solution is 0.2M or more in bivalent cation concentration.

In the method for purifying a protein of the present invention, it is preferable that the first protein is a polypeptide selected from: (a) polypeptide with the amino acid sequence represented by SEQ ID NO: 1, and (b) polypeptide with an amino acid sequence in which one or several amino acids are substituted, deleted, inserted, and/or added in the amino acid sequence represented by SEQ ID NO: 1.

In the method for purifying a protein of the present invention, it is preferable that the first protein is a polypeptide selected from: (c) polypeptide with the amino acid sequence represented by SEQ ID NO: 45, 47 or 49, and (d) polypeptide with the amino acid sequence in which one or several amino acids are substituted, deleted, inserted, and/or added in an amino acid sequence represented by SEQ ID NO: 45, 47 or 49.

A method for purifying a protein of the present invention, includes the step of: contacting a protein adsorbed to a silicon oxide-containing substance with a bivalent cation-containing solution, the protein being capable of binding to the silicon oxide-containing substance in a solution containing 0.1M sodium chloride.

In the method for purifying a protein of the present invention, it is preferable that the protein has a second protein fused therewith.

A kit for protein purification of the present invention, includes an expression vector having first DNA encoding a first protein, and an insertion site in which second DNA encoding a second protein is linked in-frame with the first DNA, the first protein being capable of binding to a silicon oxide-containing substance in a solution containing 0.1M sodium chloride.

It is preferable that the kit for protein purification of the present invention, further includes silica particles or a silica board.

It is preferable that the kit for protein purification of the present invention, further includes a bivalent cation-containing solution.

BRIEF DESCRIPTION OF DRAWINGS

FIG. 1 is an electrophoretogram showing how tightly a silica binding tag and a silica binding tag fusion protein A bind to silica.

FIG. 2 is an electrophoretogram showing how tightly a modified silica binding tag binds to silica.

FIG. 3 is an electrophoretogram of silica binding tags purified with a silica packed column.

FIG. 4 is an electrophoretogram of silica binding tags dissociated from silica particles with the use of various kinds of elution solutions.

FIG. 5 is an electrophoretogram of silica binding tags dissociated from silica particles with a $MgCl_2$ solution of various concentrations.

FIG. 6 is an electrophoretogram of silica binding tags dissociated from silica particles with the use of various kinds of bivalent cations.

FIG. 7 is an electrophoretogram for comparison between (i) purification efficiency obtained in a case where a silica binding tag fusion protein A was purified with the use of a His tag and (ii) purification efficiency obtained in a case where a silica binding tag fusion protein A was purified with the use of a silica binding tag.

DESCRIPTION OF EMBODIMENTS

Figure 1:
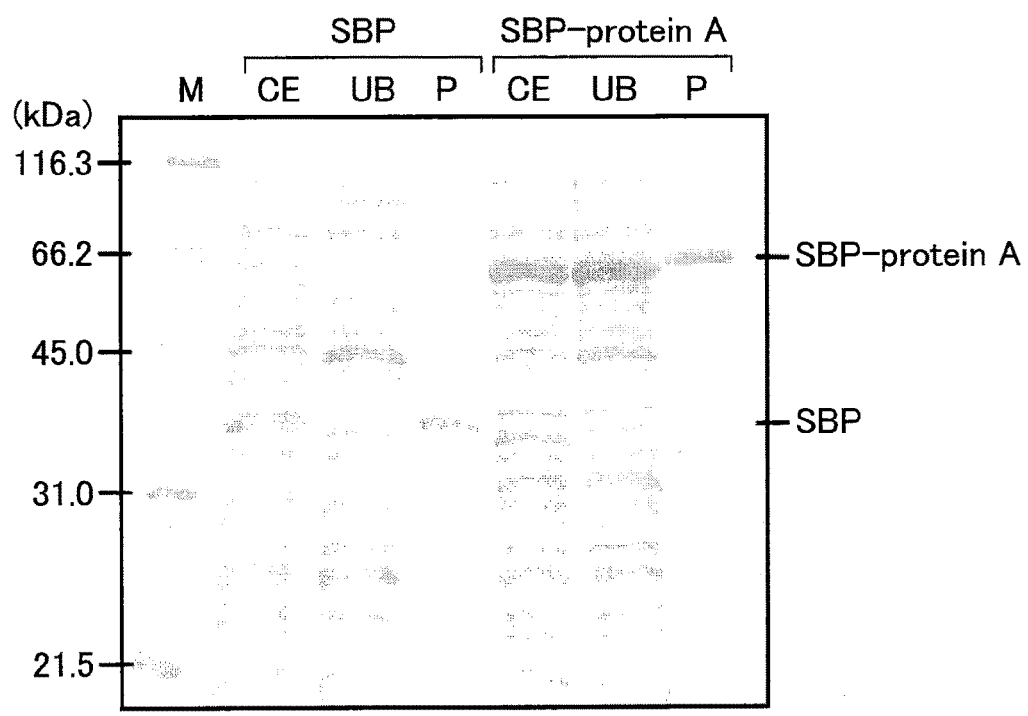
FIG. 1

The inventors of the present invention have found proteins each of which specifically binds to a silicon oxide-containing substance (see Patent Literature 1). Another protein (second protein) can be immobilized, via such a protein (first protein), on a surface of a silicon oxide-containing substance without being altered in structure and function. This time, the inventors of the present invention found a method for dissociating a protein from the silicon oxide-containing substance without damaging the structure and function of the second protein.

The term "first protein", i. e., "protein which specifically binds to a silicon oxide-containing substance" used herein refers to any "protein capable of binding to a silicon oxide-containing substance in a solution containing 0.1M sodium chloride". Further, such a protein can be derived from any organism such as bacteria, yeast, plant, or animal. For convenience of explanation, the first protein is referred to also as "SBP" (abbreviation of silicon material binding protein).

The term "silicon oxide-containing substance" used herein refers to any substance which includes oxygen (O) and silicon (S). Since elements other than oxygen and silicon are not limited to specific ones, the "silicon oxide-containing substance" may be "a substance constituted only by oxygen and silicon" or may be "a substance constituted by oxygen, silicon, and other elements". The "silicon oxide-containing substance" may be, for example, silicon dioxide (silica), glass, asbestos, quartz, crystal, silica sand, amphibole, pyroxene, mica, talc, or feldspar. The "silicon oxide-containing substance" includes an organic silicon oxide-containing substance (e.g. silicone).

The first protein used in the present invention can be any protein capable of binding to a silicon oxide-containing substance in a solution containing 0.1M sodium chloride. For example, the first protein can be obtained by adding a silicon oxide-containing substance to a protein solution (i.e. a solution containing at least one type of protein), collecting the silicon oxide-containing substance, washing the silicon oxide-containing substance in a solution containing 0.1M sodium chloride, and then isolating the protein binding to the silicon oxide-containing substance even after the washing.

A protein solution to be used can be, for example, a cell lysate, random peptide library derived from phage library, or synthesized peptide library, but is not limited to these. The protein solution can contain substances other than a protein. The protein solution may be prepared by a known method that is appropriately selected according to a material as used. For example, the cell lysate can be prepared by a method of physically disrupting cells by means of a homogenizer, ultrasonic waves, or the like, a method of disrupting cells by using an enzyme or a surface activating agent, a method of disrupting cells by a combined use of enzyme or a surface activating agent, and a physical method, or other methods.

The silicon oxide-containing substance to be added is not limited to a specific one. For example, the inventors of the present invention added 10 mg silicon powder or 5 mg asbestos (chrysotile) to a 1 ml cell lysate derived from bacteria (see Patent Literature 1). Further, the inventors of the present invention added 5 mg asbestos (chrysotile) to a 0.6 ml cell lysate derived from a mouse lung (see Patent Literature 1).

After the addition of the silicon oxide-containing substance to the protein solution, it is preferable to sufficiently mix a mixture solution of the protein and the silicon oxide-containing substance. Conditions under which the mixture solution is mixed are not limited to specific ones. For example, the mixture solution is mixed by inversion at 4° C. for 15 to 30 minutes.

The silicon oxide-containing substance can be collected by subjecting the mixture solution to centrifugation at such revolutions that allow only the silicon oxide-containing substance to precipitate, and then removing a supernatant from the mixture solution. Alternatively, the silicon oxide-containing substance can be collected by filtering the mixture solution through a filter having an appropriate pore size. However, a method for collecting the silicon oxide-containing substance is not limited to these. The collection of the silicon oxide-containing substance makes it possible to remove proteins which do not bind to the silicon oxide-containing substance.

The silicon oxide-containing substance is washed in order to remove proteins which non-specifically bind to the silicon oxide-containing substance. For example, the silicon oxide-containing substance can be washed by a method of adding a solution containing 0.1M sodium chloride to the silicon oxide-containing substance thus collected, sufficiently mixing the solution thus obtained by a method such as pipetting, and then subjecting the solution to centrifugation or filtering the solution as in the above case. Repeating this operation several times enhances a washing effect. Further, in a case where the protein solution is prepared with the use of the solution containing 0.1M sodium chloride used for washing, the washing effect (effect of removing non-specific binding) can be enhanced.

A washing solution which contains 0.1M sodium chloride can be any solution which contains 0.1M sodium chloride, and therefore is not limited to a specific one. However, the washing solution is preferably a buffer solution whose pH is around neutral. Note that the term "solution containing 0.1M sodium chloride" is intended to exclude a sodium chloride concentration of below 0.1M at which many proteins non-specifically bind to the silicon oxide-containing substance. A solution containing at least 0.1M sodium chloride is included in the "solution containing 0.1M sodium chloride".

The first protein used in the present invention can be any protein capable of binding to a silicon oxide-containing substance in a solution containing 0.1M sodium chloride. However, in a case where a sodium chloride concentration in the solution is high, it is possible to obtain a protein which more specifically binds to a silicon oxide-containing substance. For example, in order to obtain a protein which specifically binds to silica, it is preferable to use a solution containing 0.2M sodium chloride, it is more preferable to use a solution containing 0.5M sodium chloride, and it is further more preferable to use a solution containing 1M sodium chloride. For example, in order to obtain a protein which specifically binds to asbestos, it is preferable to use a solution containing 0.2M sodium chloride, and it is more preferable to use a solution containing 0.3M sodium chloride. Further, it is possible to obtain a protein which exhibits high binding specificity by adding a surface activating agent to the washing solution.

In order to obtain a bacteria-derived protein which specifically binds to silica, the inventors of the present invention used, as a washing buffer solution, 25 mM Tris-HCl buffer solution (pH 7.5) containing 1M sodium chloride and 0.5% polyoxyethylene sorbitan monolaurate (Product Name: Tween 20 (registered trademark)). Further, in order to obtain a bacteria-derived protein which specifically binds to asbestos, the inventors of the present invention used, as a washing buffering solution, 25 mM Tris-HCl buffer solution (pH 7.5) containing 0.1M sodium chloride and 0.5% polyoxyethylene sorbitan monolaurate (Product Name: Tween 20 (registered trademark)) (see Examples).

A method for isolating a protein specifically binding to a silicon oxide-containing substance from the silicon oxide-containing substance can be, for example, a method of using a surface activating agent such as dodecyl sodium salfate, a method of lowering pH, or a method of increasing a sodium chloride concentration in the solution (increasing a sodium chloride concentration to a concentration of approximately 2M), but is not limited to these. The inventors of the present invention used a solution containing 1% dodecyl sodium salfate and 2% mercaptoethanol (see Examples).

The first protein thus obtained can be identified by a known method. For example, a protein isolated from a silicon oxide-containing substance as above is separated by polyacrylamide gel electrophoresis, and is transferred on a polyvinylidene fluoride (PVDF) film. The film is stained with coomassie brilliant blue, and then a band of a target protein is cut out. A triptic digest of the band thus cut out is analyzed with the use of a matrix-assisted laser desorption/ionization time-of-flight mass spectrometer (MALDI-TOFMS), and the target protein can be identified by peptide mass fingerprint analysis. As a result, it is possible to obtain an amino acid sequence of the target protein from a known protein database. Moreover, for example, it is possible to determine an amino acid sequence with the use of an automatic peptide sequencer.

Determination of an amino acid sequence makes it possible to obtain a base sequence of a gene encoding the target protein from a known gene database, for example. Moreover, a DNA fragment encoding the target protein is cloned with a primer or a probe designed on the basis of the amino acid sequence of the target protein. Thus, it is possible to determine a base sequence with the use of a DNA sequencer.

The first protein which can be suitably used in the present invention can be a protein having the amino acid sequence represented by SEQ ID NO: 1, 3, 5, 7, 9, 11, 13, 15, 17, 19, 21, 23, 25, 27, 29, 31, 41, or 43. The inventors of the present invention identified each of these proteins as the first protein. The inventors of the present invention found out for the first time that each of these proteins, which are all known proteins, is capable of specifically binding to a silicon-oxide containing substance.

Among these eighteen proteins, a protein having the amino acid sequence represented by SEQ ID NO: 1, 3, 5, 7, 9, or 11 is a protein identified by the inventors of the present invention as a protein which specifically binds to silica, and a protein having the amino acid sequence represented by SEQ ID NO: 13, 15, 17, 19, 21, 23, 25, 27, 29, 31, 41 or 43 is a protein identified by the inventors of the present invention as a protein which specifically binds to asbestos.

Further, a protein which (i) has the amino acid sequence having deletion, substitution, or addition of one or several amino acids in the amino acid sequence represented by SEQ ID NO: 1, 3, 5, 7, 9, 11, 13, 15, 17, 19, 21, 23, 25, 27, 29, 31, 41, or 43 and (ii) is capable of binding to a silicon oxide-containing substance in a solution containing 0.1M sodium chloride can be suitably used in the present invention. The meaning of the wording "deletion, substitution, or addition of one or several amino acids" is described later.

The first protein used in the present invention can be produced by subjecting a cell serving as a supply source of the first protein to incubation which is followed by isolating and purifying processes. Further, the first protein can be produced by establishing a recombinant expression vector by a known genetic engineering method and by incorporating the recombinant expression vector into a suitable host cell so that it is expressed as a recombinant protein.

The present invention is described below with reference to an embodiment in which silica is used as a silicon oxide-containing substance and a ribosomal protein L2 is used as the first protein (a protein which specifically binds to a silicon oxide-containing substance). A person skilled in the art will easily understand that the present invention is not limited to this embodiment. All of the academic literatures and patent literatures mentioned in this specification are hereby incorporated by reference.

A protein purifying method of the present embodiment includes the step of dissociating a fusion protein of a ribosomal protein L2 and a second protein from silica with the use of a bivalent cation-containing solution. That is, according to the protein purifying method of the present embodiment, the ribosomal protein L2 is specifically dissociated from silica with the use of a bivalent cation in order to purify a target fusion protein.

The ribosomal protein L2 is a protein that was found by the inventors of the present invention to specifically bind to silica (silicon dioxide, $SiO_2$). The term "protein" used herein is interchangeable with "polypeptide" or "peptide". The term "protein" includes a fragment of a protein. Further, the term "protein" includes a fusion protein. The term "fusion protein" is a protein in which fragments or whole of two or more heteroproteins are fused.

The ribosomal protein L2 may be derived from any organism such as bacteria, yeast, plant, or animal, or may be artificially synthesized. Specifically, the ribosomal protein L2 may be selected from:

(a) polypeptide having the amino acid sequence represented by SEQ ID NO: 1, and (b) polypeptide having the amino acid sequence in which one or several amino acids are substituted, deleted, inserted, and/or added in the amino acid sequence represented by SEQ ID NO: 1.

Alternatively, the ribosomal protein L2 may be selected from:

(c) polypeptide having the amino acid sequence represented by SEQ ID NO: 45, 47, or 49;

(d) polypeptide having the amino acid sequence one or several amino acids are substituted, deleted, inserted, and/or added in the amino acid sequence represented by SEQ ID NO: 45, 47 or 49.

Note that the polypeptide having the amino acid sequence represented by SEQ ID NO: 1 corresponds to an entire length of the ribosomal protein L2, and the polypeptide having the amino acid sequence represented by SEQ ID NO: 45 or 47 corresponds to a section of the ribosomal protein L2 which is necessary for adsorption to silica (corresponds to positions 1 through 60 or positions 204 through 273 of the amino acid sequence represented by SEQ ID NO: 1). A protein having the section corresponding to positions 1 through 60 or positions 204 through 273 in the amino acid sequence represented by SEQ ID NO: 1 can continue to be adsorbed to silica. That is, a ribosomal protein L2 which can be used in the present invention is a fragment of polypeptide having the amino acid sequence represented by SEQ ID NO: 1. The fragment is a protein including positions 1 through 60 or positions 204 through 273 in the amino acid sequence represented by SEQ ID NO: 1. Alternatively, the ribosomal protein L2 which can be used in the present invention may be fusion polypeptide of (i) polypeptide including positions 1 through 60 of the amino acid sequence represented by SEQ ID NO: 1 and (ii) polypeptide including positions 204 through 273 of the amino acid sequence represented by SEQ ID NO: 1 (that is, the ribosomal protein L2 may be polypeptide having the amino acid sequence represented by SEQ ID NO. 49). In this specification, the ribosomal protein L2 which can be used in the present invention indicates polypeptide capable of specifically binding to silica, and is referred to also as "silica binding tag". Further, the wording "binding" can be used instead of "adsorption" of a protein to silica.

The wording "one or several amino acids are substituted, deleted, inserted, and/or added" means that amino acids as many as can be substituted, deleted, inserted, and/or added by a known mutant peptide producing method such as a site-specific mutagenesis (preferably not more than 10, more preferably not more than 7, and further preferably not more than 5). Such a mutant protein is not limited to a protein that is artificially mutated by a known mutant polypeptide producing method, and therefore may be obtained by isolating and purifying a naturally existing protein.

It is well known in the art that some amino acids in an amino acid sequence of a protein can be easily modified without significantly affecting a structure or a function of the protein. It is also known in the art that mutation occurs not only in an artificially modified protein, but also in a naturally existing protein without causing a significant change in structure and function of the protein. The mutation preferably includes substitution, deletion, insertion, and/or addition of amino acid which is conservative or non-conservative. Silent substitution, addition, and deletion are preferable, and conservative substitution is particularly preferable.

Typical examples of conservative substitution include substitution of one of aliphatic amino acids Ala, Val, Leu, and Ile with another amino acid, exchange of hydroxyl residues Ser and Thr, exchange of acidic residues Asp and Glu, substitution between amide residues Asn and Gln, exchange of basic residues Lys and Arg, and substitution between aromatic residues Phe and Tyr.

The term "second protein" used herein mainly refers to a protein to be purified, and is used interchangeably with "target protein". An arrangement of the second protein is not limited to a specific one, and therefore a desired protein can be used as the second protein.

Next, a method for fusing together a ribosomal protein L2 and a second protein is described.

The method for fusing together a ribosomal protein L2 and a second protein may be any method which enables strong fusion between the ribosomal protein L2 and the second protein, and is therefore not limited to a specific one. The ribosomal protein L2 and the second protein can be fused together in any bonding manners such as covalent bond, hydrophobic bond, ion bond, hydrogen bond, and a combination of these. The covalent bond is preferably used since it can produce stronger fusion between the ribosomal protein L2 and the second protein.

For example, a ribosomal protein L2 and a second protein may be fused together with the use of a cross-linking agent. Such a cross-linking agent is not limited to a specific one, and therefore can be any known cross-linking agent. For example, such a cross-linking agent preferably is dimethyl suberoimidate dihydrochloride (DMS), suberic acid di-N-hydroxysuccinimide ester (DSS), tartaric acid N-hydroxydisuccinimide ester (DST), p-phenylene bismaleimide (pPDM), methyl 4-mercaptobutylimidate hydrochloride (MBI), or methyl 4-azidebenzoimidate hydrochloride (ABI), but is not limited to these. With this arrangement, it is possible to realize strong fusion between a ribosomal protein L2 and a second protein. It is preferable to adopt this arrangement especially in a case where both of ribosomal protein L2 and second protein are easily obtainable proteins. A method for fusing together a ribosomal protein L2 and a second protein with the use of a cross-linking agent can be a known method appropriately selected in accordance with the type of the cross-linking agent.

Alternatively, fusion between a ribosomal protein L2 and a second protein can be carried out by causing both of the ribosomal protein L2 and the second protein to be expressed as a fusion protein with the use of an expression vector. With this arrangement, it is possible to easily produce a fusion protein in which the ribosomal protein L2 and the second protein are fused. As a result, it is possible to easily purify wide variety of proteins in large amount.

An arrangement of the expression vector is not limited to a specific one, provided that it includes a base sequence encoding a fusion protein of a ribosomal protein L2 and a second protein. The expression vector may be any vector which can express a fusion protein in a host. For example, the expression vector can be produced by using plasmid, phage, or cosmid.

The expression vector has a tag sequence encoding a ribosomal protein L2 in a base sequence encoding a fusion protein. The tag sequence may be:

(e) polynucleotide having the base sequence represented by SEQ ID NO: 2, or (f) polynucleotide which hybridizes the base sequence represented by SEQ ID NO: 2 or a base sequence that is complementary to the base sequence represented by SEQ ID NO: 2 under a stringent condition.

The expression vector has a tag sequence encoding a ribosomal protein L2 in a base sequence encoding a fusion protein. The tag sequence may be:

(g) polynucleotide having the base sequence represented by SEQ ID NO: 46, 48, or 50, or (h) polynucleotide which hybridizes the base sequence represented by SEQ ID NO: 46, 48, or 50 or a base sequence that is complementary to the base sequence represented by SEQ ID NO: 2 under a stringent condition.

Note that the polynucleotide having the base sequence represented by SEQ ID NO: 2 corresponds to an entire length of the ribosomal protein L2, and the polynucleotide having the base sequence represented by SEQ ID NO: 46 or 48 corresponds to a section of the ribosomal protein L2 which is necessary for adsorption to silica (corresponds to positions 1 through 60 or positions 204 through 273 of the amino acid sequence represented by SEQ ID No: 1). Further, polynucleotide having the base sequence represented by SEQ ID NO: 50 corresponds to fusion polypeptide of (i) the section of the ribosomal protein L2 (positions 1 through 60 of the amino acid sequence represented by SEQ ID NO: 1) and the section of the ribosomal protein L2 (positions 204 through 273 of the amino acid sequence represented by SEQ ID NO: 1).

The wording "stringent condition" means that hybridization will occur only if there is at least 90%, preferably 95%, or most preferably 97% identity between the sequences.

The hybridization can be carried out by a known method such as a method described in "Molecular Cloning: A Laboratory Manual 3rd Edition, J. Sambrook and D. W. Russell, Cold Spring Harbor Laboratory, NY (2001)". In general, the higher the temperature becomes, or the lower the salt concentration becomes, the higher the stringency becomes (the more difficult the hybridization becomes) so that more homologous polynucleotide can be obtained.

A promoter appropriate for a host is selected and is inserted in an expression vector, and a base sequence encoding a fusion protein is inserted at a downstream of the promoter.

The expression vector preferably contains an expression control region (e.g., promoter, terminator, and/or replication origin) depending on the type of a host to be introduced. For example, a conventional promoter (e.g., trc promoter, tac promoter, lac promoter) is preferably used as a promoter of an expression vector for bacteria. For example, a glyceraldehyde 3-phosphate dehydrogenase promoter or a PH05 promoter is preferably used as a promoter of an expression vector for yeast. For example, an amylase promoter or a trpC promoter is preferably used as a promoter of an expression vector for filamentous fungi. A viral promoter (e.g., SV40 early promoter, SV40 late promoter) is preferably used as a promoter of an expression vector for animal cells.

An expression vector can be produced by a conventional method using restriction enzyme and/or ligase. Moreover, transformation of a host by an expression vector can be carried out by a conventional method.

The expression vector preferably includes at least one selective marker. Such a selective marker is not limited to a specific one. However, in a case where an eukaryotic cell is used as a host, dihydrofolate reductase or neomycin resistant gene is preferably used as such a selective marker. Further, in a case where *E. coli* or other bacteria is used as a host, tetracycline resistance gene or ampicilin resistant gene is preferably used as such a selective marker.

The selective marker is used to confirm whether the expression vector has been introduced in a host, and whether a fusion protein has been expressed in a host.

Such a host is not limited to a specific one. For example, the following conventionally known cells can be used: bacteria such as *Escherichia coli*, yeast (budding yeast (*Saccharomyces cerevisiae*), fission yeast (*Schizosaccharomyces pombe*)), nematode (*Caenorhabditis elegans*), oocyte of an African clawed frog (*Xenopus laevis*), animal cells (e.g., CHO cell, COS cell, NIH3T3 cell, Bowes melanoma).

A method for introducing an expression vector into a host, namely a method for transforming a host is not limited to a specific one. A conventionally known method such as electroporation, calcium phosphate method, liposome method, or DEAE dextran method can be suitably used as such a method.

A ribosomal protein L2 can be fused with a second protein at any position. For example, the ribosomal protein L2 can be fused with an amino acid at the N terminal of the second protein, an amino acid at the C terminal of the second protein, or amino acids between the N terminal and the C terminal. In a case where the aforementioned expression vector is used, the ribosomal protein L2 is preferably fused with the N terminal or C terminal of the second protein. With this arrangement, it is possible to simplify a structure of the expression vector and to easily insert various kinds of base sequences encoding various kinds of second proteins into the expression vector.

The second protein thus fused with the ribosomal protein L2 is firmly adsorbed to silica (silicon dioxide, $SiO_2$). Silica to which a protein is adsorbed is not limited to a specific form. For example, the silica preferably has a particle shape or a board shape. Note that it is unnecessary that the whole of the particle or the board is made of silica, but it is only necessary that at least a part of the particle or the board is made of silica. For example, in a case where a column is formed with the use of particle-shaped silica, it is possible to more easily purify the second protein. Moreover, use of the particle-shaped silica makes it possible to easily obtain a second protein adsorbed to silica by centrifugation. Further, use of board-shaped silica not only makes it possible to purify a protein, but also makes it possible to easily produce various kinds of boards on which proteins are immobilized (e.g. semiconductor substrate in which a silicon substrate is used).

A way in which a fusion protein of a ribosomal protein L2 and a second protein is adsorbed to silica is not limited to a specific one. For example, adsorption of the fusion protein to silica is preferably accomplished by mixing the fusion protein and silica in a solution.

Such a solution is not limited to a specific one, but for example, preferably is a NaCl solution with high concentration. Concentration of NaCl in the solution is not limited to a specific one, but for example, preferably is 0.5M to 5M, more preferably is 0.5M to 2.5M, most preferably is 1M to 2M. Since, according to this arrangement, a fusion protein is fused with silica under extremely high NaCl concentration, it is possible to prevent substances other than the fusion protein from binding to silica. In other words, with this arrangement, it is possible to purify a fusion protein to high purity.

Such a solution preferably contains a surface activating agent. The surface activating agent is not limited to a specific one, but preferably is polyoxyethylene sorbitan monolaurate, dodecyl sodium sulfate, cholic acid, or deoxycholic acid. With this arrangement, it is possible to purify a fusion protein of a ribosomal protein L2 and a second protein to higher purity.

A protein purifying method of the present embodiment includes the step of dissociating a fusion protein of a ribosomal protein L2 and a second protein from silica with the use of a bivalent cation-containing solution.

The bivalent cation-containing solution is not limited to a specific one, but preferably is a $MgCl_2$ solution, a $CaCl_2$ solution, or $NiCl_2$ solution, further preferably is a $MgCl_2$ solution or a $CaCl_2$ solution, and most preferably is a $MgCl_2$ solution, for example. With this arrangement, it is possible to specifically dissociate a fusion protein of a ribosomal protein L2 and a second protein from silica.

Concentration of bivalent cation in the bivalent cation-containing solution is not limited to a specific one, but preferably is 0.2M or more, further preferably is 1M or more, and most preferably is 2M or more, for example. With this arrangement, it is possible to more effectively dissociate a fusion protein of a ribosomal protein L2 and a second protein from silica.

The step of dissociating a fusion protein from silica may be carried out, for example, by centrifugation or a column method. As for the centrifugation, for example, silica to which a fusion protein is adsorbed is dispersed in a bivalent cation-containing solution. Next, the solution in which silica is dispersed is subjected to centrifugation, so that the fusion protein dissociated from silica can be obtained in a supernatant. As for the column method, a column is filled with silica to which a fusion protein is adsorbed. The fusion protein is eluted from the column with the use of a bivalent cation-containing solution.

In this way, a fusion protein dissociated from silica can be easily obtained.

A fusion protein dissociated from silica contains bivalent cation (e.g. $MgCl_2$) in high concentration. In view of this, the protein purifying method of the present embodiment preferably includes the step of removing the bivalent cation in accordance with the intended use. The bivalent cation may be removed by any method. However, for example, the bivalent cation is preferably removed by dialysis. With this arrangement, it is possible to more highly purify a protein.

Moreover, the protein purifying method of the present embodiment preferably includes, before the dissociating step, the step of washing silica so that a fusion protein of a ribosomal protein L2 and a second protein is not dissociated from silica. The step of washing silica is not limited to a specific one. However, for example, the washing of silica is preferably carried out with the use of a highly-concentrated NaCl solution. Concentration of NaCl in the solution is not limited in particular, but preferably is 0.5M to 5M, more preferably is 2M to 5M, and most preferably is 2M. With this arrangement, it is possible to effectively remove substances other than the second protein which is adsorbed to silica. In other words, with this arrangement, it is possible to highly purify a protein.

The solution preferably contains a surface activating agent. The surface activating agent is not limited to a specific one, but preferably is polyoxyethylene sorbitan monolaurate, dodecyl sodium sulfate, cholic acid, or deoxycholic acid. With this arrangement, it is possible to more highly purify a protein.

As described above, the present invention provides a novel protein purifying method.

The present invention makes it possible to highly purify a large amount of proteins capable of binding to silica. As such, the present invention can be applied to a wide variety of field such as manufacture of a protein chip, a nano-biodevice, or a medical product. Since a protein produced by the method of the present invention is capable of binding to silica, the present invention can be applied especially to manufacture of a semiconductor.

EXAMPLES

[1. Construction of Silica Binding Tag Fusion Protein A (SBP-protein A) Expression Vector]

Two types of oligonucleotide primers (primer 1, primer 2) were produced based on a sequence of a protein A gene (spa) derived from *Staphylococcus aureus subsp. aureus* MW2.

```
                                        (SEQ ID NO: 33)
Primer 1: 5'-ATCGAATTCTGCGCAACACGATGAAGCTCAAC-3'

(SEQ ID NO: 34)
Primer 2: 5'-GTTGAGCTCGTGTTGTTGTCTTCCTCTTTTG-3'
```

The protein A gene was amplified by a PCR method with the use of the primer 1 and the primer 2 by using chromosomal DNA of *Staphylococcus aureus subsp. aureus* MW2 as a template. The PCR reaction was performed using KOD Plus DNA polymerase (TOYOBO) according to TOYOBO's protocol. Note that, in the base sequences of the primers, "GAATTC" is an EcoRI recognition site, and "GAGCTC" is a SacI recognition site.

Products obtained by the PCR reaction and expression vector pET21-b (Novagen) were digested with the use of restriction enzymes EcoRI and SacI at 37° C. for two hours. Subsequently, DNA fragments thus amplified and pET21-b were purified by agarose gel electrophoresis. The DNA fragments and pET21-b thus purified were ligated with the use of Ligation High (TOYOBO) at 16° C. for two hours.

The expression vector thus obtained was used to transform *Escherichia coli* MV1184. From a colony of *E. coli* thus obtained, an expression vector into which a target DNA fragment was inserted was selected. The expression vector was named as pET-SpA.

Next, two types of oligonucleotide primers (primer 3, primer 4) were produced based on a sequence of a ribosomal protein L2 gene (rp1B) derived from *E. coli* K12.

```
                                        (SEQ ID NO: 35)
   Primer 3:   5'-GTTGTCGACATGGCAGTTGTTAAATGAA-3'

(SEQ ID NO: 36)
   Primer 4:   5'-GTTGCGGCCGCTTTGCTACGGCGACGTACG-3'
```

The ribosomal protein L2 gene was amplified by a PCR method with the use of the primer 3 and the primer 4 by using chromosomal DNA of *E. coli* K12 as a template. The PCR reaction was performed using KOD Plus DNA polymerase (TOYOBO) according to TOYOBO's protocol. Note that, in the base sequences of the primers, "GTCGAC" is a SalI recognition site, and "GCGGCCGC" is a NotI recognition site.

Products obtained by the PCR reaction and expression vector pET-SpA were digested with the use of restriction enzymes SalI and NotI at 37° C. for two hours. Subsequently, DNA fragments thus amplified and pET-SpA were purified by agarose gel electrophoresis. The DNA fragments and pET-SpA thus purified were ligated with the use of Ligation High (TOYOBO) at 16° C. for two hours.

The expression vector thus obtained was used to transform *E. coli* MV1184. From a colony of *E. coli* thus obtained, an expression vector into which a target DNA fragment was inserted was selected. The expression vector was named as pET-SpA-Sitag.

[2. Construction of Silica Binding Tag (SBP) Expression Vector]

Two types of oligonucleotide primers (primer 3, primer 4) were produced based on a sequence of a ribosomal protein L2 gene (rp1B) derived from *E. coli* K12.

Primer 5: 5'-CATCGAATTCTATGGCAGTTGTTAAATGTAAA-3' (SEQ ID NO: 37)

Primer 6: 5'-AGTTGAGCTCGTTTTGCTACGGCGACGTACGA-3' (SEQ ID NO: 38)

The ribosomal protein L2 gene was amplified by a PCR method with the use of the primer 5 and the primer 6 by using chromosomal DNA of *E. coli* K12 as a template. The PCR reaction was performed using KOD Plus DNA polymerase (TOYOBO) according to TOYOBO's protocol. Note that, in the base sequences of the primers, "GAATTC" is a EcoRI recognition site, and "GAGCTC" is a SacI recognition site.

Products obtained by the PCR reaction and expression vector pET21-b (Novagen) were digested with the use of restriction enzymes EcoRI and SacI at 37° C. for two hours. Subsequently, DNA fragments thus amplified and pET21-b were purified by agarose gel electrophoresis. The DNA fragments and pET21-b thus purified were ligated with the use of Ligation High (TOYOBO) at 16° C. for two hours.

The expression vector thus obtained was used to transform *E. coli* MV1184. From a colony of *E. coli* thus obtained, an expression vector into which a target DNA fragment was inserted was selected. The expression vector was named as pET-L2N.

[3. Construction of Modified Silica Binding Tag (1-60) Expression Vector]

Two types of oligonucleotide primers (primer 7, primer 8) were produced based on a sequence of a ribosomal protein L2 gene (rp1B) derived from *E. coli* K12.

Primer 7: 5'-AGTAATGCTAGCGCAGTTGTTAAATGTAAACCG-3' (SEQ ID NO: 39)

Primer 8: 5'-ACAATCTCGAGTTACTGCTTGTGGCC-3' (SEQ ID NO: 40)

A region of the ribosomal protein L2 gene which corresponds to 60 residues of the N terminal was amplified by a PCR method with the use of the primer 7 and the primer 8 by using chromosomal DNA of *E. coli* K12 as a template. The region is polynucleotide represented by SEQ ID NO: 46. The polynucleotide encodes polypeptide represented by SEQ ID NO: 45. The PCR reaction was performed using KOD Plus DNA polymerase (TOYOBO) according to TOYOBO's protocol. Note that, in the base sequences of the primers, "GCTAGC" is a NheI recognition site, and "CTCGAG" is a XhoI recognition site.

Products obtained by the PCR reaction and expression vector pET21-b (Novagen) were digested with the use of restriction enzymes NheI and XhoI at 37° C. for two hours. Subsequently, DNA fragments thus amplified and pET21-b were purified by agarose gel electrophoresis. The DNA fragments and pET21-b thus purified were ligated with the use of Ligation High (TOYOBO) at 16° C. for two hours.

The expression vector thus obtained was used to transform *E. coli* JM109. From a colony of *E. coli* thus obtained, an expression vector into which a target DNA fragment was inserted was selected. The expression vector was named as pET-L2 (1-60).

[4. Purification of Silica Binding Tag, Modified Silica Binding Tag, and Silica Binding Tag Fusion Protein A Using Silica]

The pET-L2N, pET-L2 (1-60), pET-SpA-Sitag were used to produce a silica binding tag, a modified silica binding tag, and a silica binding tag fusion protein A, respectively. Each of these proteins were purified with the use of silica particles. The following description deals with this process.

First, *E. coli* to which the vectors were introduced was incubated at 37° C. Note that the introduction of the vectors to the *E. coli* was carried out by a known method. When $OD_{600}$ reached 0.6, IPTG was added so that the final concentration became 0.5 mM. Four hours after the addition of IPTG, the *E. coli* was collected by centrifugation.

The *E. coli* was suspended in a disrupting solution (2M: NaCl, 0.5% (v/v): surface activating agent (Tween 20), 25 mM: Tris-HCl (pH 8.0)). Subsequently, the *E. coli* was disrupted by an ultrasonic treatment.

After the disruption of the *E. coli*, the disrupting solution was subjected to centrifugation (24000×g, 15 minutes) so that a supernatant was collected. Note that the supernatant is referred to as "bacteria extraction solution (CE)" in FIG. 1. Note also that "M" in FIG. 1 indicates a molecular-weight marker.

Silica particles (silicon dioxide fine powder ca. 0.8 μm, SOEKAWA CHEMICAL Co., Ltd.) were added to the supernatant. The resulting solution was mixed at 4° C. for 30 minutes.

After the mixing, the silica particles were collected by centrifugation (3000×g, 5 minutes). Note that a supernatant obtained by this centrifugation is referred to as "silica unbound fraction (UB)" in FIG. 1. The silica particles thus collected were washed twice with the disrupting solution.

The silica particles thus washed were suspended in a 100 mM Tris-HCl buffer solution containing 2M $MgCl_2$. The resulting solution was stirred at 4° C. for 10 minutes. Thus, proteins binding to silica were dissociated from silica. After the stirring, the silica particles were precipitated by centrifugation (3000×g, 5 minutes). Subsequently, a supernatant obtained by this centrifugation was collected. Note that the supernatant is referred to as "elution protein fraction (P)" in FIG. 1.

FIG. 1 is an electrophoretogram showing how strongly each of a silica binding tag and a silica binding tag fusion protein A binds to silica.

As shown in FIG. 1, it has been revealed that a silica binding tag is dissociated from silica with the use of 2M $MgCl_2$. It has also been revealed that the elution protein fraction (P) contains a silica binding tag (SBP) or a silica binding tag fusion protein (SBP-protein A) with high purity of approximately 90%.

Moreover, removal of $MgCl_2$ in the elution protein fraction (P) by dialysis caused a silica binding protein or a fusion protein contained in the elution protein fraction (P) to bind to silica again. That is, it has been revealed that a degree of binding between a silica binding tag and silica can be reversibly adjusted by adjusting concentration of $MgCl_2$.

Figure 2:
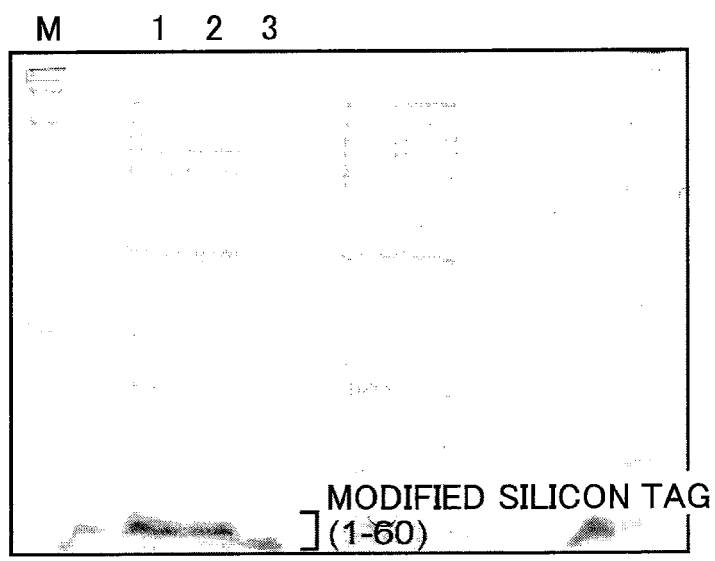
FIG. 2

FIG. 2 is an electrophoretogram showing how strongly a modified silica binding tag binds to silica. Note that the lane 1 indicates a modified silica binding tag in the bacteria extraction solution (CE), the lane 2 indicates a modified silica binding tag in the silica unbound fraction (UB), and the lane 3 indicates a modified silica binding tag in the elution protein fraction (P).

It is preferable that a size of a tag used for purifying a protein is as small as possible. As shown in FIG. 2, a size of a modified silica binding tag is approximately 60 amino acids, and is therefore very small as compared to an original silica binding tag. However, it has been revealed that the modified silica binding tag can be suitably used as a tag used for purifying a protein since the modified silica binding tag is purified to high purity (approximately 90%) as shown in FIG. 2.

[5. Purification of Silica Binding Tag Using Silica Packed Column]

Silica particles (diameter: 0.1 μm, approximately 800 mg, QUARTRON SP-03B, FUSO CHEMICAL CO., LTD.) were packed in a commercially available empty column (Tricorn 5/20; GE Healthcare). Thus, a silica packed column was obtained. The silica packed column was sufficiently washed with the use of Milli-Q water and a washing solution (25 mM Tris-HCl (pH 8.0), 0.5M NaCl, 0.5% Tween 20). Subsequently, an extract of E. coli (0.45 g wet cells of E. coli) in which a silica binding tag was expressed was added to the silica packed column at a flow rate of 0.5 mL/min.

Figure 3:
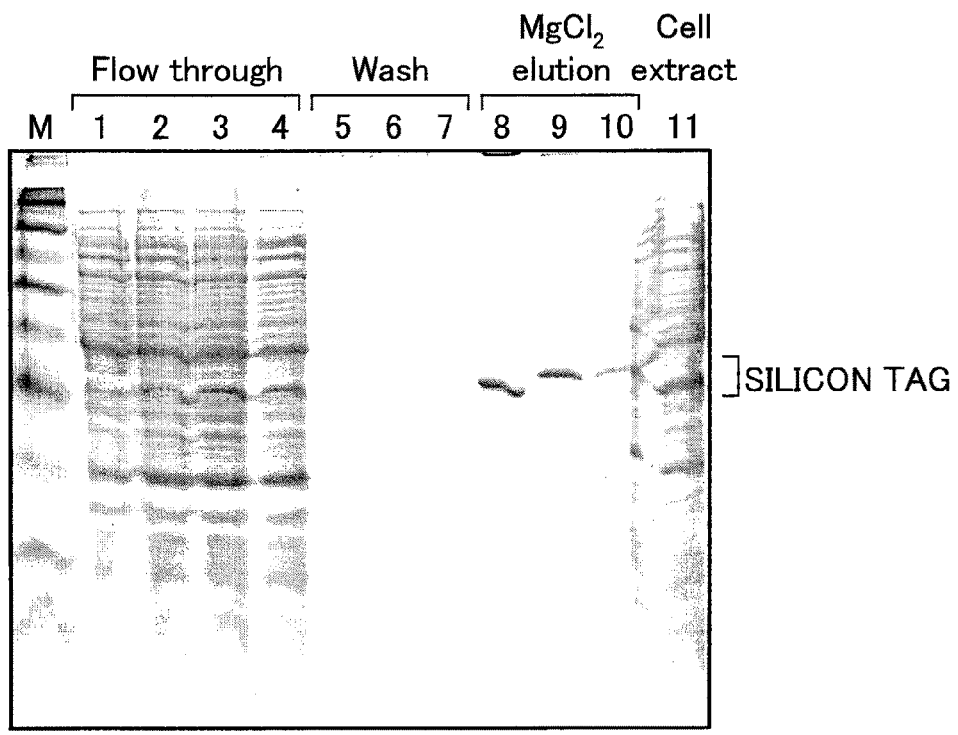
FIG. 3

The silica packed column was washed with a 5 mL washing solution. Subsequently, a 100 mM Tris-HCl (pH 8.0) buffer solution containing 2M $MgCl_2$ was added to the silica packed column so that the silica binding tag was eluted. FIG. 3 is an electrophoretogram of a silica binding tag purified with the silica packed column.

As shown in FIG. 3, a silica binding tag could be purified to high purity (approximately 90%).

[6. Conditions under which Silica Binding Tag is Dissociated]

A study was conducted as to conditions under which a silica binding tag was dissociated from silica particles.

First, a 10 μg silica binding tag purified by column chromatography and 10 mg silica particles were added to a 1 mL buffer solution (25 mM Tris-HCl (pH 8.0), 2M NaCl, 0.5% (v/v) Tween 20). The resulting solution was mixed at 4° C. for 30 minutes.

Subsequently, silica particles to which the silica binding tag bound were collected by centrifugation (12000×g, 1 minute, 4° C.). The silica particles thus collected were washed twice with the use of the buffer solution. Various kinds of elution solutions were added to the silica particles thus washed. The resulting solution was mixed for 5 minutes. Subsequently, a supernatant was removed by centrifugation.

To the remaining silica particles, a 30 μl sample buffer for SDS-PAGE was added. The resulting solution was heated at 100° C. for 5 minutes. Thus, the silica binding tag remaining on the silica particles was dissociated in the sample buffer. Subsequently, the sample buffer in which the silica binding tag was dissociated was subjected to SDS-PAGE (12.5%).

Figure 4:
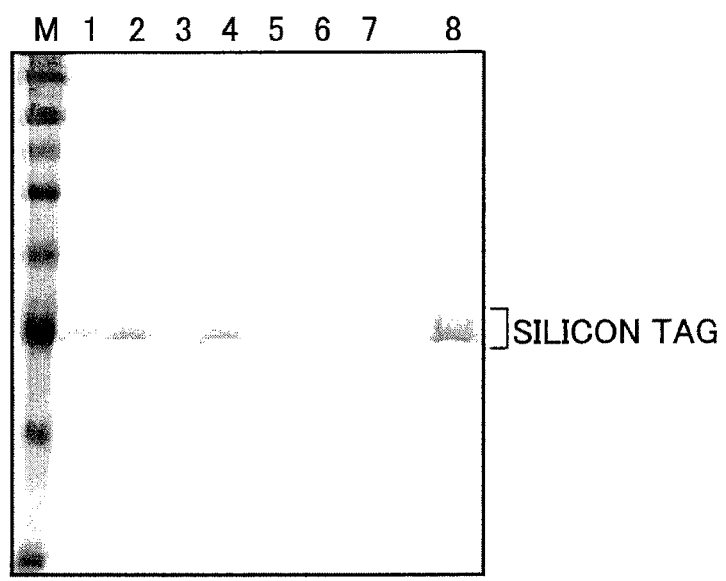
FIG. 4

FIG. 4 shows the result of the SDS-PAGE. In FIG. 4, the lane 1 indicates a silica binding tag binding to silica particles in a case where an elution solution was not used (negative control), the lane 2 indicates a silica binding tag remaining on silica particles in a case where a 5M NaCl solution was used as an elution solution, the lane 3 indicates a silica binding tag remaining on silica particles in a case where a 100 mM Tris-HCl (pH 8.0) buffer solution containing 2M $MgCl_2$ was used as an elution solution, the lane 4 indicates a silica binding tag remaining on silica particles in a case where a CHAPS-NaOH (pH12) buffer solution was used as an elution solution, the lane 5 indicates a silica binding tag remaining on silica particles in a case where a 1N NaOH solution was used as an elution solution, the lane 6 indicates a silica binding tag remaining on silica particles in a case where a $CH_3COOH$—NaOH (pH 4.26) was used as an elution solution, the lane 7 indicates a silica binding tag remaining on silica particles in a case where a 1N HCl solution was used as an elution solution, and the lane 8 indicates a purified silica binding tag which was used in this experiment.

As shown in FIG. 4, it was proved that a silica binding tag is dissociated from silica particles in a case where an acid solution such as a 1N HCl solution or an alkali solution such as a 1N NaOH solution is used as an elution solution (see the lane 5 or lane 7, for example). However, such a condition causes protein denaturation. Consequently, it is impossible to purify a protein without losing the activity of the protein. It is necessary to dissociate a silica binding tag under a neutral condition in order to dissociate a protein having a silica binding tag from silica particles without losing the activity of the protein. In view of this, a study was conducted as to whether or not it is possible to dissociate a silica binding tag by using various kinds of ions.

It was impossible to dissociate a silica binding tag from silica particles in a case where a high concentration NaCl solution, which has been conventionally used as an elution liquid, was used as an elution solution. It was impossible to dissociate a silica binding tag from silica particles even with a NaCl solution whose concentration was increased to 5M (see the lane 2).

In contrast, it was proved that it is possible to dissociate a silica binding tag from silica particles in a case where a 100 mM Tris-HCl (pH 8.0) buffer solution containing 2M $MgCl_2$ is used as an elution solution (see the lane 3).

[7. Concentration of $MgCl_2$ in Elution Solution]

Escherichia coli to which pET-L2N was introduced was incubated in 2×YT medium. When $OD_{600}$ reached 0.6, IPTG was added so that the final concentration became 0.5 mM.

Four hours after the addition of IPTG, the incubated E. coli was collected by centrifugation (6000×g, 15 minutes, 4° C.). The E. coli thus collected was suspended in a buffer solution (25 mM Tris-HCl (pH 8.0)), and was then disrupted by an ultrasonic treatment.

The resulting solution was subjected to centrifugation (40000×g, 20 minutes, 4° C.) to obtain a supernatant. The supernatant was determined as a bacteria disrupted solution. 500 μL of the bacteria disrupted solution and 10 mg silica particles were added to a 1 mL buffer solution (25 mM Tris-HCl (pH8.0), 2M NaCl, 0.5% (v/v) Tween 20). The resulting solution was mixed at 4° C. for 30 minutes.

Subsequently, silica particles to which a silica binding tag bound were collected by centrifugation (12000×g, 1 minute, 4° C.). The silica particles thus collected were washed twice with the use of the buffer solution. Various kinds of elution solutions were added to the silica particles thus washed. The resulting solution was mixed for 5 minutes. Subsequently, a supernatant and a pellet of the silica particles were separately collected by centrifugation.

A sample buffer was added to a part of the supernatant and the silica particles. The samples were subjected to SDS-PAGE (12.5%).

The remaining supernatant was mixed with silica particles again so that a silica binding tag bound to the silica particles. Subsequently, second elution was carried out by the same method as above. This is to confirm whether a degree of purification was improved by carrying out purification steps twice.

Figure 5:
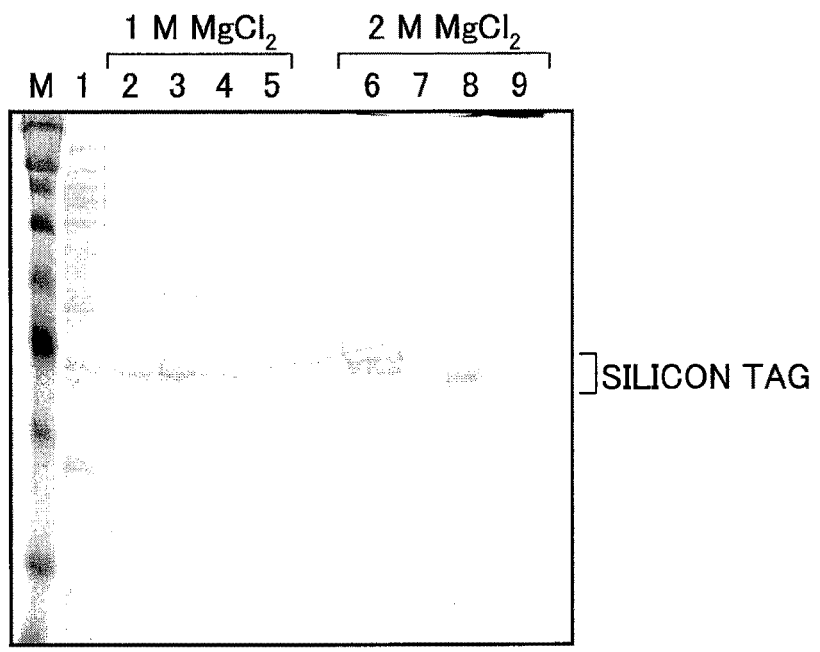
FIG. 5

FIG. 5 shows the result of the SDS-PAGE. In FIG. 5, the lane 1 indicates a silica binding tag contained in an E. coli disrupted solution, each of the lanes 2 to 5 indicates a silica binding tag obtained in a case where a 100 mM Tris-HCl (pH 8.0) buffer solution containing 1M $MgCl_2$ was used as an elution solution, and each of the lanes 6 to 9 indicates a silica binding tag obtained in a case where a 100 mM Tris-HCl (pH 8.0) buffer solution containing 2M $MgCl_2$ was used as an elution solution. More specifically, each of the lanes 2 and 6 indicates a silica binding tag contained in the first elution fraction (supernatant), and each of the lanes 3 and 7 indicates a silica binding tag remaining on silica particles after the first elution. Further, each of the lanes 4 and 8 indicates a silica binding tag contained in the second elution fraction (supernatant), and each of the lanes 5 and 9 indicates a silica binding tag remaining on silica particles after the second elution.

As shown in FIG. 5, it was proved that it is possible to dissociate a silica binding tag even by using 1M $MgCl_2$ (see the lane 2). It was proved that, in this case, the silica binding tag partially remains on the silica particles (see the lane 3)

In contrast, it was proved that, in a case where 2M $MgCl_2$ is used, almost all of the silica binding tag can be dissociated from the silica particles (see the lane 6) without remaining on the silica particles (see the lane 7).

It was proved that a silica binding tag can be purified to 90% purity or more with only one purifying operation, thereby making it unnecessary to carry out the purifying operation twice.

[8. Dissociation Effect of Bivalent Cation Other Than $Mg^{2+}$]

A study was conducted as to whether or not it is possible to dissociate a silica binding tag from silica particles with the use of bivalent cation other than $Mg^{2+}$. An experiment was carried out in accordance with the method described in [7. Concentration of $MgCl_2$ in Elution Solution]. The inventors of the present invention tried to study dissociation effect of a $CaCl_2$ solution, a $NiCl_2$ solution, a $FeCl_2$ solution, a $ZnCl_2$ solution, and a $MnCl_2$ solution. However, preparation of a 2M $FeCl_2$ solution, a 2M $ZnCl_2$ solution, and a 2M $MnCl_2$ solution in a Tris buffer solution caused a precipitate. Therefore, only dissociation effect of a 2M $CaCl_2$ solution and a 2M $NiCl_2$ solution was studied.

Figure 6:
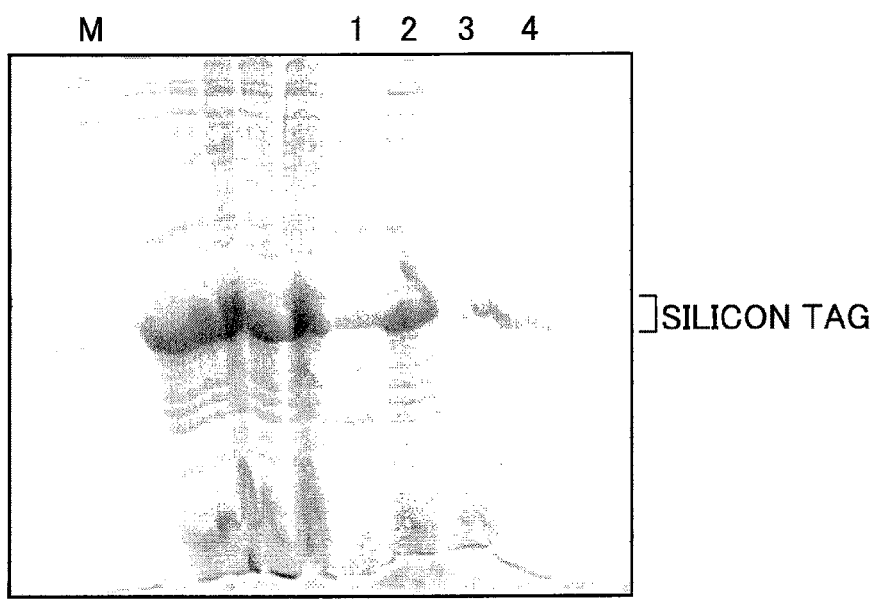
FIG. 6

FIG. 6 shows a result of SDS-PAGE. In FIG. 6, the lane 1 indicates a silica binding tag which remained on silica particles in a case where a $CaCl_2$ solution was used as an elution solution, the lane 2 indicates a silica binding tag which remained on silica particles in a case where a $NiCl_2$ solution was used as an elution solution, the lane 3 indicates a silica binding tag contained in an elution solution in a case where a $CaCl_2$ solution was used as the elution solution, and the lane 4 a silica binding tag contained in an elution solution in a case where a $NiCl_2$ solution was used as the elution solution.

As shown in FIG. 6, it has been revealed that a silica binding tag can be dissociated from silica particles with the use of either $CaCl_2$ solution or $NiCl_2$ solution. It has been also revealed that each of $CaCl_2$ solution and $NiCl_2$ solution is inferior to a $MgCl_2$ solution in dissociation effect (elution effect) of a silica binding tag.

[9. Affinity Purifying Method Using Silica Binding Tag and Comparison with Affinity Purifying Method Using His Tag]

E. coli into which an expression vector pET-SpA-Si tag was introduced was incubated at 37° C. Note that the expression vector was introduced into the E. coli by a known method.

When $OD_{600}$ reached 0.6, IPTG was added to the incubation solution so that the final concentration became 0.5 mM. Four hours after the addition of IPTG, the E. coli was collected by centrifugation.

A silica binding tag fusion protein A expressed in the E. coli had two kinds of tags for purification, i.e., a silica binding tag and a His tag, each of which was fused with a protein A. A comparison was carried out in purification efficiency between the silica binding tag and the His tag by carrying out purification using the silica binding tag and purification using the His tag.

E. coli was suspended in a disrupting solution (25 mM Tris-HCl (pH 8.0), 2M NaCl, 0.5% (v/v) surface activating agent Tween 20 (registered trademark)). Subsequently, the E. coli was disrupted by an ultrasonic treatment. After the disruption of the E. coli, the disrupting solution was subjected to centrifugation (24000×g, 15 minutes) to obtain a supernatant.

For purification using the His tag, a HisTrap HP 1 mL column (manufactured by GE Healthcare biosciences) was used. Note that the purification was basically carried out in accordance with the GE Healthcare biosciences' protocol. To put it simply, the column was equilibrated with a buffer solution (20 mM sodium phosphate (pH 7.4), 0.5M NaCl, 5 mM imidazole), and then the supernatant obtained by the centrifugation was added to the column. The column was washed with the use of the buffer solution. Subsequently, a target protein was eluted with gradient elution from 5 mM to 500 mM imidazole.

As for purification using the silica binding tag, silica particles (Silicon dioxide fine powder ca. 0.8 μm, SOEKAWA CHEMICAL Co., Ltd.) were added to the supernatant obtained by the centrifugation. The resulting solution was mixed at 4° C. for 30 minutes. After the mixing, the silica particles were collected by centrifugation (3000×g, 5 minutes). The silica particles thus collected were washed with the disrupting solution twice. The silica particles thus washed were suspended in a 100 mM Tris-HCl buffer solution containing 2M $MgCl_2$. The suspension was stirred at 4° C. for 10 minutes. Thus, proteins binding to silica were dissociated from the silica. After the stirring, the silica particles were precipitated by centrifugation (3000×g, 5 minutes). Subsequently, a supernatant was collected.

Figure 7:
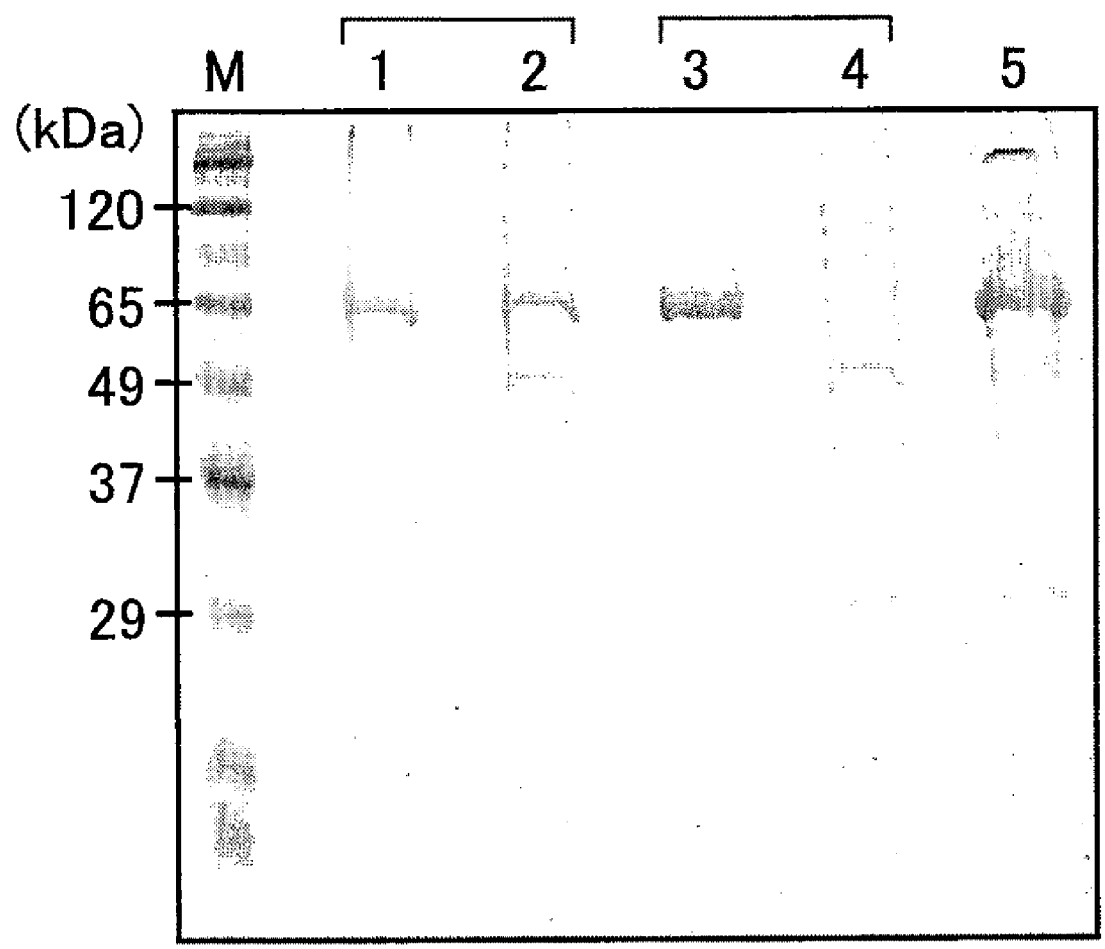
FIG. 7

FIG. 7 shows a result obtained by subjecting proteins purified with the His tag and proteins purified with the silica binding tag to SDS-PAGE (12.5%). In FIG. 7, the lane 1 indicates a purification fraction obtained with the use of a HisTrap column, the lane 2 indicates a HisTrap column unbound fraction, the lane 3 indicates a purification fraction obtained with the use of a silica binding tag, the lane 4 indicates a silica particle unbound fraction, the lane 5 indicates a supernatant of an E. coli disrupted solution which is obtained before purification (supernatant obtained by centrifugation), and the lane M indicates a molecular weight marker.

Analysis using image analysis software Image J revealed that a target protein obtained through purification using the His tag was 93% in purity and 77% in yield (see the lane 1). On the other hand, a protein obtained through purification using the silica binding tag was 85% in purity and 93% in yield (see the lane 3). That is, it was possible to purify a target protein with high purity comparable to that of conventional affinity purification and with high yield.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. A method for purifying a protein, comprising the step of:
contacting a fusion protein of a first protein and a second protein with a bivalent cation-containing solution, the fusion protein being adsorbed to the silicon oxide component of a silicon oxide-containing substance, the first protein being capable of binding to the silicon oxide-containing substance in a solution containing 0.1 M sodium chloride, wherein the fusion protein dissociates from the silicon oxide-containing substance after the fusion protein is contacted with the bivalent cation-containing solution.

2. The method for purifying a protein according to claim 1, further comprising the step of:
adsorbing the fusion protein to the silicon oxide-containing substance.

3. The method for purifying a protein according to claim 2, further comprising the step of:
expressing the fusion protein in a transformant.

4. The method for purifying a protein according to claim 3, further comprising the step of:
  causing second DNA encoding the second protein to be linked in-frame with first DNA encoding the first protein.

5. The method for purifying a protein according to claim 1, wherein:
  the bivalent cation-containing solution is a $MgCl_2$ solution, a $CaCl_2$ solution or a $NiCl_2$ solution.

6. The method for purifying a protein according to claim 1, wherein:
  the bivalent cation-containing solution is 0.2M or more in bivalent cation concentration.

7. The method for purifying a protein according to claim 1, wherein:
  the first protein is a polypeptide selected from:
    (a) polypeptide with the amino acid sequence represented by SEQ ID NO: 1, and
    (b) polypeptide with an amino acid sequence in which one or several amino acids are substituted, deleted, inserted, and/ or added in the amino acid sequence represented by SEQ ID NO: 1.

8. The method for purifying a protein according to claim 1, wherein:
  the first protein is a polypeptide selected from:
    (c) polypeptide with the amino acid sequence represented by SEQ ID NO: 45, 47 or 49, and
    (d) polypeptide with an amino acid sequence in which one or several amino acids are substituted, deleted, inserted, and/or added in the amino acid sequence represented by SEQ ID NO: 45, 47 or 49.

9. A method for purifying a protein, comprising the step of:
  contacting a protein adsorbed to the silicon oxide component of a silicon oxide-containing substance with a bivalent cation-containing solution,
  the protein being capable of binding to the silicon oxide-containing substance in a solution containing 0.1M sodium chloride, wherein the protein dissociates from the silicon oxide-containing substance after the protein is contacted with the bivalent cation-containing solution.

* * * * *

SEQUENCE LISTING

<160> NUMBER OF SEQ ID NOS: 50

<210> SEQ ID NO 1
<211> LENGTH: 273
<212> TYPE: PRT
<213> ORGANISM: Escherichia coli

<400> SEQUENCE: 1

Met Ala Val Val Lys Cys Lys Pro Thr Ser Pro Gly Arg Arg His Val
1               5                   10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly His Lys Gln Ala Tyr Arg Ile
    50                  55                  60

Val Asp Phe Lys Arg Asn Lys Asp Gly Ile Pro Ala Val Val Glu Arg
65                  70                  75                  80

Leu Glu Tyr Asp Pro Asn Arg Ser Ala Asn Ile Ala Leu Val Leu Tyr
                85                  90                  95

Lys Asp Gly Glu Arg Arg Tyr Ile Leu Ala Pro Lys Gly Leu Lys Ala
            100                 105                 110

Gly Asp Gln Ile Gln Ser Gly Val Asp Ala Ala Ile Lys Pro Gly Asn
        115                 120                 125

Thr Leu Pro Met Arg Asn Ile Pro Val Gly Ser Thr Val His Asn Val
130                 135                 140

Glu Met Lys Pro Gly Lys Gly Gly Gln Leu Ala Arg Ser Ala Gly Thr
145                 150                 155                 160

Tyr Val Gln Ile Val Ala Arg Asp Gly Ala Tyr Val Thr Leu Arg Leu
                165                 170                 175

Arg Ser Gly Glu Met Arg Lys Val Glu Ala Asp Cys Arg Ala Thr Leu
            180                 185                 190

Gly Glu Val Gly Asn Ala Glu His Met Leu Arg Val Leu Gly Lys Ala
        195                 200                 205

Gly Ala Ala Arg Trp Arg Gly Val Arg Pro Thr Val Arg Gly Thr Ala
    210                 215                 220

Met Asn Pro Val Asp His Pro His Gly Gly Gly Glu Gly Arg Asn Phe
225                 230                 235                 240

Gly Lys His Pro Val Thr Pro Trp Gly Val Gln Thr Lys Gly Lys Lys
                245                 250                 255

Thr Arg Ser Asn Lys Arg Thr Asp Lys Phe Ile Val Arg Arg Arg Ser
            260                 265                 270

Lys

<210> SEQ ID NO 2
<211> LENGTH: 822
<212> TYPE: DNA
<213> ORGANISM: Escherichia coli

<400> SEQUENCE: 2
atggcagttg ttaaatgtaa accgacatct ccgggtcgtc gccacgtagt taaagtggtt     60
aaccctgagc tgcacaaggg caaacctttt gctccgttgc tggaaaaaaa cagcaaatcc    120
ggtggtcgta acaacaatgg ccgtatcacc actcgtcata tcggtggtgg ccacaagcag    180
gcttaccgta ttgttgactt caaacgcaac aaagacggta tcccggcagt tgttgaacgt    240

```
cttgagtacg atccgaaccg ttccgcgaac atcgcgctgg ttctgtacaa agacggtgaa    300
cgccgttaca tcctggcccc taaaggcctg aaagctggcg accagattca gtctggcgtt    360
gatgctgcaa tcaaaccagg taacaccctg ccgatgcgca acatcccggt tggttctact    420
gttcataacg tagaaatgaa accaggtaaa ggcggtcagc tggcacgttc cgctggtact    480
tacgttcaga tcgttgctcg tgatggtgct tatgtcaccc tgcgtctgcg ttctggtgaa    540
atgcgtaaag tagaagcaga ctgccgtgca actctgggcg aagttggcaa tgctgagcat    600
atgctgcgcg ttctgggtaa agcaggtgct gcacgctggc gtggtgttcg tccgaccgtt    660
cgcggtaccg cgatgaaccc ggtagaccac ccacatggtg gtggtgaagg tcgtaacttt    720
ggtaagcacc cggtaactcc gtggggcgtt cagaccaaag gtaagaagac ccgcagcaac    780
aagcgtactg ataaattcat cgtacgtcgc cgtagcaaat aa                      822
```

<210> SEQ ID NO 3
<211> LENGTH: 273
<212> TYPE: PRT
<213> ORGANISM: Pseudomonas aeruginosa

<400> SEQUENCE: 3

```
Met Ala Ile Val Lys Cys Lys Pro Thr Ser Ala Gly Arg Arg Phe Val
1               5                   10                  15

Val Lys Val Val Asn Gln Glu Leu His Lys Gly Ala Pro Tyr Ala Pro
            20                  25                  30

Leu Leu Glu Lys Lys Ser Lys Ser Gly Gly Arg Asn Asn Asn Gly Arg
        35                  40                  45

Ile Thr Thr Arg His Ile Gly Gly His Lys Gln His Tyr Arg Leu
    50                  55                  60

Val Asp Phe Arg Arg Asn Lys Asp Gly Ile Pro Ala Ile Val Glu Arg
65                  70                  75                  80

Val Glu Tyr Asp Pro Asn Arg Thr Ala His Ile Ala Leu Leu Lys Tyr
                85                  90                  95

Ala Asp Gly Glu Arg Arg Tyr Ile Ile Ala Pro Lys Gly Val Ala Ala
            100                 105                 110

Gly Asp Gln Leu Ile Ser Gly Ile Gly Ala Pro Ile Lys Ala Gly Asn
        115                 120                 125

Ser Met Pro Leu Arg Asn Ile Pro Val Gly Ser Thr Val His Gly Ile
130                 135                 140

Glu Leu Lys Pro Gly Lys Gly Ala Gln Ile Ala Arg Ser Ala Gly Ala
145                 150                 155                 160

Ser Ala Gln Leu Val Ala Arg Glu Gly Ala Tyr Val Thr Leu Arg Leu
                165                 170                 175

Arg Ser Gly Glu Met Arg Lys Val Leu Ala Glu Cys Arg Ala Thr Leu
            180                 185                 190

Gly Glu Val Ser Asn Ser Glu His Ser Leu Arg Ser Leu Gly Lys Ala
        195                 200                 205

Gly Ala Thr Arg Trp Arg Gly Val Arg Pro Thr Val Arg Gly Val Ala
    210                 215                 220

Met Asn Pro Val Asp His Pro His Gly Gly Gly Glu Gly Arg Thr Ser
225                 230                 235                 240

Ala Gly Arg His Pro Val Ser Pro Trp Gly Leu Gln Thr Lys Gly Lys
                245                 250                 255

Lys Thr Arg Ser Asn Lys Arg Thr Asp Asn Met Ile Val Arg Arg Arg
            260                 265                 270
```

Lys

<210> SEQ ID NO 4
<211> LENGTH: 822
<212> TYPE: DNA
<213> ORGANISM: Pseudomonas aeruginosa

<400> SEQUENCE: 4

| | | | | | |
|---|---|---|---|---|---|
| atggcaatcg | ttaagtgcaa | accgacttcc | gctggtcgtc | gctttgtcgt | caaggtggtg | 60 |
| aatcaggagc | tgcacaaagg | cgctccctac | gcaccgctgc | tggaaaagaa | atccaagtct | 120 |
| ggcggccgta | caacaacgg | tcgtatcacc | accgtcata | tcggtggtgg | tcacaagcag | 180 |
| cactaccgtc | tggtcgactt | ccgtcgcaac | aaggatggca | tccctgccat | cgttgagcgc | 240 |
| gtcgaatacg | atccgaaccg | cactgcacac | atcgctctgc | tgaagtatgc | agacggcgag | 300 |
| cgtcgctaca | tcatcgcccc | caagggcgtt | gctgcaggtg | accagctgat | ctccggtatc | 360 |
| ggtgcgccga | tcaaggcagg | caacagcatg | cctctgcgca | catcccggt | gggtagcact | 420 |
| gttcatggta | tcgagctgaa | gccgggtaaa | ggcgctcaga | tcgctcgctc | cgctggcgct | 480 |
| tccgcccagc | tggtcgcgcg | tgaaggtgcg | tacgtaaccc | tgcgtctgcg | ctccggtgaa | 540 |
| atgcgtaaag | tcctggctga | gtgccgtgcg | accctgggcg | aagtctcgaa | ctccgagcac | 600 |
| agcctgcgtt | cgctgggtaa | agccggtgct | acgcgctggc | gtggtgttcg | cccgaccgtt | 660 |
| cgcggcgtgg | cgatgaaccc | ggtcgaccac | ccgcatggtg | gtggtgaagg | ccgtacctct | 720 |
| gctggtcgtc | atccggtatc | gccgtggggt | cttcagacca | agggtaagaa | gactcgctcg | 780 |
| aacaagcgta | ccgataacat | gatcgtccgc | cgccgcaagt | aa | | 822 |

<210> SEQ ID NO 5
<211> LENGTH: 350
<212> TYPE: PRT
<213> ORGANISM: Pseudomonas aeruginosa

<400> SEQUENCE: 5

Met Lys Leu Lys Asn Thr Leu Gly Val Val Ile Gly Ser Leu Val Ala
1               5                   10                  15

Ala Ser Ala Met Asn Ala Phe Ala Gln Gly Gln Asn Ser Val Glu Ile
                20                  25                  30

Glu Ala Phe Gly Lys Arg Tyr Phe Thr Asp Ser Val Arg Asn Met Lys
            35                  40                  45

Asn Ala Asp Leu Tyr Gly Gly Ser Ile Gly Tyr Phe Leu Thr Asp Asp
        50                  55                  60

Val Glu Leu Ala Leu Ser Tyr Gly Glu Tyr His Asp Val Arg Gly Thr
65                  70                  75                  80

Tyr Glu Thr Gly Asn Lys Lys Val His Gly Asn Leu Thr Ser Leu Asp
                85                  90                  95

Ala Ile Tyr His Phe Gly Thr Pro Gly Val Gly Leu Arg Pro Tyr Val
            100                 105                 110

Ser Ala Gly Leu Ala His Gln Asn Ile Thr Asn Ile Asn Ser Asp Ser
        115                 120                 125

Gln Gly Arg Gln Gln Met Thr Met Ala Asn Ile Gly Ala Gly Leu Lys
    130                 135                 140

Tyr Tyr Phe Thr Glu Asn Phe Ala Lys Ala Ser Leu Asp Gly Gln
145                 150                 155                 160

Tyr Gly Leu Glu Lys Arg Asp Asn Gly His Gln Gly Glu Trp Met Ala
                165                 170                 175

Gly Leu Gly Val Gly Phe Asn Phe Gly Gly Ser Lys Ala Ala Pro Ala

|     |     |     |     | 180 |     |     |     | 185 |     |     |     | 190 |     |     |
| --- | --- | --- | --- | --- | --- | --- | --- | --- | --- | --- | --- | --- | --- | --- |

Pro Glu Pro Val Ala Asp Val Cys Ser Asp Ser Asp Asn Asp Gly Val
        195                 200                 205

Cys Asp Asn Val Asp Lys Cys Pro Asp Thr Pro Ala Asn Val Thr Val
        210                 215                 220

Asp Ala Asn Gly Cys Pro Ala Val Ala Glu Val Val Arg Val Gln Leu
225                 230                 235                 240

Asp Val Lys Phe Asp Phe Asp Lys Ser Lys Val Lys Glu Asn Ser Tyr
                245                 250                 255

Ala Asp Ile Lys Asn Leu Ala Asp Phe Met Lys Gln Tyr Pro Ser Thr
            260                 265                 270

Ser Thr Thr Val Glu Gly His Thr Asp Ser Val Gly Thr Asp Ala Tyr
        275                 280                 285

Asn Gln Lys Leu Ser Glu Arg Arg Ala Asn Ala Val Arg Asp Val Leu
    290                 295                 300

Val Asn Glu Tyr Gly Val Glu Gly Arg Val Asn Ala Val Gly Tyr
305                 310                 315                 320

Gly Glu Ser Arg Pro Val Ala Asp Asn Ala Thr Ala Glu Gly Arg Ala
                325                 330                 335

Ile Asn Arg Arg Val Glu Ala Glu Val Glu Ala Glu Ala Lys
            340                 345                 350

<210> SEQ ID NO 6
<211> LENGTH: 1053
<212> TYPE: DNA
<213> ORGANISM: Pseudomonas aeruginosa

<400> SEQUENCE: 6

```
atgaaactga agaacacctt aggcgttgtc atcggctcgc tggttgccgc ttcggcaatg      60
aacgcctttg cccagggcca gaactcggta gagatcgaag ccttcggcaa gcgctacttc     120
accgacagcg ttcgcaacat gaagaacgcg gacctgtacg cgggctcgat cggttacttc     180
ctgaccgacg acgtcgagct ggcgctgtcc tacggtgagt accatgacgt tcgtggcacc     240
tacgaaaccg gcaacaagaa ggtccacggc aacctgacct ccctggacgc catctaccac     300
ttcggtaccc cgggcgtagg tctgcgtccg tacgtgtcgg ctggtctggc tcaccagaac     360
atcaccaaca tcaacagcga cagccaaggc cgtcagcaga tgaccatggc caacatcggc     420
gctggtctga gtactacttc caccgagaac ttcttcgcca aggccagcct cgacggccag     480
tacggtctgg agaagcgtga caacggtcac cagggcgagt ggatggctgg cctgggcgtc     540
ggcttcaact cggtggtttc gaaagccgct ccggctccgg aaccggttgc gacgtttgc      600
tccgactccg acaacgacgg cgtttgcgac aacgtcgaca gtgcccgga taccccggcc      660
aacgtcaccg ttgacgccaa cggctgcccg gctgtcgccg aagtcgtacg cgtacagctg     720
gacgtgaagt tcgacttcga caagtccaag gtcaaagaga acagctacgc tgacatcaag     780
aacctggctg acttcatgaa gcagtacccg tccacttcca ccaccgttga aggtcacacc     840
gactccgtcg gcaccgacgc ttacaaccag aagctgtccg agcgtcgtgc caacgccgtt     900
cgtgacgtac tggtcaacga gtacggtgta gaaggtggtc gcgtgaacgc tgttggttac     960
ggcgagtccc gcccggttgc cgacaacgcc accgctgaag ccgcgctat caaccgtcgc    1020
gttgaagccg aagtagaagc tgaagccaag taa                                 1053
```

<210> SEQ ID NO 7
<211> LENGTH: 274
<212> TYPE: PRT

<213> ORGANISM: Pseudomonas putida

<400> SEQUENCE: 7

Met Ala Ile Val Lys Cys Lys Pro Thr Ser Pro Gly Arg Arg Phe Val
1               5                   10                  15

Val Lys Val Val Asn Lys Glu Leu His Lys Gly Ala Pro His Ala Pro
            20                  25                  30

Leu Ile Glu Lys Lys Ser Lys Ser Gly Gly Arg Asn Asn Asn Gly Arg
        35                  40                  45

Ile Thr Thr Arg His Val Gly Gly His Lys Gln His Tyr Arg Leu
    50                  55                  60

Val Asp Phe Arg Arg Asn Asp Lys Asp Gly Ile Pro Ala Thr Val Glu
65                  70                  75                  80

Arg Ile Glu Tyr Asp Pro Asn Arg Thr Ala His Ile Ala Leu Leu Cys
                85                  90                  95

Tyr Ala Asp Gly Glu Arg Arg Tyr Ile Ile Ala Pro Lys Gly Val Ser
            100                 105                 110

Ala Gly Asp Gln Leu Ile Ala Gly Ala Leu Ala Pro Ile Lys Ala Gly
        115                 120                 125

Asn Ser Leu Gln Leu Arg Asn Ile Pro Val Gly Ser Thr Ile His Gly
130                 135                 140

Ile Glu Leu Lys Pro Gly Lys Gly Ala Gln Ile Ala Arg Ser Ala Gly
145                 150                 155                 160

Ala Ser Ala Gln Leu Ile Ala Arg Glu Gly Val Tyr Val Thr Leu Arg
                165                 170                 175

Leu Arg Ser Gly Glu Met Arg Lys Val Leu Ala Glu Cys Arg Ala Thr
            180                 185                 190

Leu Gly Glu Val Ser Asn Ser Glu His Ser Leu Arg Ser Leu Gly Lys
        195                 200                 205

Ala Gly Ala Lys Arg Trp Arg Gly Val Arg Pro Thr Val Arg Gly Val
210                 215                 220

Ala Met Asn Pro Val Asp His Pro His Gly Gly Glu Gly Arg Thr
225                 230                 235                 240

Ser Gly Gly Arg His Pro Val Ser Pro Trp Gly Phe Pro Thr Lys Gly
                245                 250                 255

Ala Lys Thr Arg Gly Asn Lys Arg Thr Asp Asn Met Ile Val Arg Arg
            260                 265                 270

Arg Lys

<210> SEQ ID NO 8
<211> LENGTH: 825
<212> TYPE: DNA
<213> ORGANISM: Pseudomonas putida

<400> SEQUENCE: 8
atggcaatcg ttaaatgcaa accgacttcc cctggccgcc gtttcgtggt caaggtggtc      60
aacaaggagc tgcacaaagg cgctcctcac gcaccgctga tcgagaaaaa atcgaagtct     120
ggtggtcgta acaacaatgg ccgcattacc actcgtcacg ttggtggtgg tcacaagcag     180
cattaccgtc tggtcgactt ccgtcgcaac gacaaagatg gcattccagc cactgtcgag     240
cgtatcgaat acgatccaaa ccgtactgct cacatcgccc tgctgtgcta cgcagacggt     300
gagcgtcgct acatcatcgc gcctaaaggc gtgagcgctg gcgaccagct gatcgcaggt     360
gccctggccc caatcaaggc cggtaactcc ctgcagctgc gcaacattcc agtaggtagc     420
accattcacg gcatcgaact gaagccgggt aaaggtgctc agatcgctcg ttccgctggt     480

```
gcttcggctc agctgatcgc tcgcgaaggt gtctacgtga ccctgcgtct gcgctctggt    540
gaaatgcgta aagtcctggc tgagtgccgt gcgaccctgg gcgaagtctc gaactccgag    600
cacagcctgc gttcgctggg taaagctggt gccaaacgct ggcgcggcgt tcgcccaacc    660
gttcgtggtg ttgccatgaa cccggttgac cacccacacg tggtggtga aggtcgtacc     720 tccggtggtc gtcatccggt atcgccatgg gcttcccaa ccaagggtgc taaaacccgt     780
ggtaataagc gtaccgacaa catgatcgtc cgtcgtcgca agtaa                    825
```

<210> SEQ ID NO 9
<211> LENGTH: 245
<212> TYPE: PRT
<213> ORGANISM: Pseudomonas putida

<400> SEQUENCE: 9

```
Met Ser Gln Val Asn Met Arg Asp Met Leu Lys Ala Gly Val His Phe
 1               5                  10                  15

Gly His Gln Thr Arg Tyr Trp Asn Pro Lys Met Gly Lys Tyr Ile Phe
             20                  25                  30

Gly Ala Arg Asn Lys Ile His Ile Val Asn Leu Glu Lys Thr Leu Pro
         35                  40                  45

Met Phe Asn Asp Ala Leu Ser Phe Val Glu Arg Leu Ala Gln Gly Lys
     50                  55                  60

Asn Lys Ile Leu Phe Val Gly Thr Lys Arg Ser Ala Gly Lys Ile Val
 65                  70                  75                  80

Ala Glu Gln Ala Ala Arg Cys Gly Ser Pro Tyr Val Asp His Arg Trp
                 85                  90                  95

Leu Gly Gly Met Leu Thr Asn Tyr Lys Thr Ile Arg Ala Ser Ile Lys
            100                 105                 110

Arg Leu Arg Asp Leu Glu Thr Gln Ala Glu Asp Gly Thr Phe Ala Lys
        115                 120                 125

Leu Thr Lys Lys Glu Ala Leu Met Arg Ser Arg Asp Leu Glu Lys Leu
    130                 135                 140

Asp Arg Ser Leu Gly Gly Ile Lys Asp Met Gly Gly Leu Pro Asp Ala
145                 150                 155                 160

Leu Phe Val Ile Asp Val Asp His Glu Arg Ile Ala Ile Thr Glu Ala
                165                 170                 175

Asn Lys Leu Gly Ile Pro Val Ile Gly Val Val Asp Thr Asn Ser Ser
            180                 185                 190

Pro Glu Gly Val Asp Tyr Ile Ile Pro Gly Asn Asp Asp Ala Ile Arg
        195                 200                 205

Ala Ile Glu Leu Tyr Met Thr Ser Met Ala Asp Ala Val Ile Arg Gly
    210                 215                 220

Arg Asn Asn Val Ala Gly Gly Thr Glu Val Tyr Ala Glu Glu Ala Ala
225                 230                 235                 240

Ala Pro Ala Ala Glu
            245
```

<210> SEQ ID NO 10
<211> LENGTH: 738
<212> TYPE: DNA
<213> ORGANISM: Pseudomonas putida

<400> SEQUENCE: 10

```
atgtcccaag tcaacatgcg cgatatgctg aaggccggtg tgcacttcgg ccaccagacc    60
cgttactgga acccgaaaat gggcaagtac attttcggcg cgcgtaacaa gatccacatc    120
```

```
gtcaacctgg aaaaaaccct gccaatgttc aacgacgctc tgtcgttcgt agagcgcctg        180
gcccagggca agaacaagat cctgttcgtc ggcaccaagc gttccgccgg caagatcgtc        240
gccgagcaag cagctcgttg cggttcgccg tacgttgacc accgttggtt gggcggcatg        300
ctgaccaact acaagaccat ccgcgcttcg atcaagcgtc tgcgcgacct ggaaacccag        360
gccgaagacg gcactttcgc caagctgacc aagaaagaag ccctgatgcg ctcccgcgac        420
ctggaaaaac tggatcgcag cctgggtggc atcaaggaca tgggcggtct gccagacgct        480
ctgttcgtta tcgacgttga tcacgagcgc atcgcgatca ccgaagccaa caaactgggt        540
atcccggtca tcggcgttgt cgataccaac agcagcccgg aaggtgttga ctacatcatc        600
ccaggtaacg atgacgccat cgcgctatc gagctgtaca tgacttcgat ggctgacgca        660
gtcatccgcg gccgcaacaa cgttgccggc ggcaccgaag tttacgctga agaagcggct        720
gcacctgctg ctgagtaa                                                     738

<210> SEQ ID NO 11
<211> LENGTH: 130
<212> TYPE: PRT
<213> ORGANISM: Pseudomonas putida

<400> SEQUENCE: 11

Met Ser Ala Thr Gln Asn Tyr Gly Thr Gly Arg Arg Lys Thr Ala Thr
1               5                   10                  15

Ala Arg Val Phe Leu Arg Pro Gly Thr Gly Asn Ile Ser Ile Asn Asn
            20                  25                  30

Arg Ser Leu Asp Val Phe Phe Gly Arg Glu Thr Ala Arg Met Val Val
        35                  40                  45

Arg Gln Pro Leu Glu Leu Thr Glu Ser Val Glu Lys Phe Asp Ile Tyr
    50                  55                  60

Val Thr Val Ser Gly Gly Gly Val Ser Gly Gln Ala Gly Ala Ile Arg
65                  70                  75                  80

His Gly Ile Thr Arg Ala Leu Met Glu Tyr Asp Glu Thr Leu Arg Gly
                85                  90                  95

Ala Leu Arg Arg Ala Gly Tyr Val Thr Arg Asp Ala Arg Glu Val Glu
            100                 105                 110

Arg Lys Lys Val Gly Leu Arg Lys Ala Arg Lys Arg Pro Gln Tyr Ser
        115                 120                 125

Lys Arg
    130

<210> SEQ ID NO 12
<211> LENGTH: 393
<212> TYPE: DNA
<213> ORGANISM: Pseudomonas putida

<400> SEQUENCE: 12
atgtcggcga ctcaaaatta cggcactggc cgtcgcaaga ccgcaaccgc tcgcgtattc        60
ctgcgtccgg gtactggtaa catttccatc aacaaccgtt ctctggacgt gttcttcggt       120
cgcgaaaccg ctcgcatggt tgttcgccag ccgctcgagc tgactgaatc cgttgagaaa       180
ttcgacatct acgtcaccgt ttccggtggt ggtgtcagcg gtcaggccgg tgcgatccgt       240
cacggtatca cccgcgctct gatggaatac gacgaaaccc tgcgtggcgc tctgcgtcgt       300
gctggctacg tcacccgcga cgctcgtgaa gttgagcgta agaaagtggg tctgcgtaaa       360
gcgcgtaagc gtcctcagta ctccaagcgt taa                                    393
```

<210> SEQ ID NO 13
<211> LENGTH: 638
<212> TYPE: PRT
<213> ORGANISM: Escherichia coli

<400> SEQUENCE: 13

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
370                 375                 380

```
Asp Val Lys Asp Val Leu Leu Leu Asp Val Thr Pro Leu Ser Leu Gly
385                 390                 395                 400

Ile Glu Thr Met Gly Val Met Thr Thr Leu Ile Ala Lys Asn Thr
            405                 410                 415

Thr Ile Pro Thr Lys His Ser Gln Val Phe Ser Thr Ala Glu Asp Asn
                420                 425                 430

Gln Ser Ala Val Thr Ile His Val Leu Gln Gly Glu Arg Lys Arg Ala
            435                 440                 445

Ala Asp Asn Lys Ser Leu Gly Gln Phe Asn Leu Asp Gly Ile Asn Pro
        450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Gly Asp His Leu Leu His
530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln His Ala Gln
        595                 600                 605

Gln Gln Thr Ala Gly Ala Asp Ala Ser Ala Asn Asn Ala Lys Asp Asp
    610                 615                 620

Asp Val Val Asp Ala Glu Phe Glu Glu Val Lys Asp Lys Lys
625                 630                 635

<210> SEQ ID NO 14
<211> LENGTH: 1917
<212> TYPE: DNA
<213> ORGANISM: Escherichia coli

<400> SEQUENCE: 14
atgggtaaaa taattggtat cgacctgggt actaccaact cttgtgtagc gattatggat      60
ggcaccactc ctcgcgtgct ggagaacgcc gaaggcgatc gcaccacgcc ttctatcatt     120
gcctataccc aggatggtga aactctagtt ggtcagccgg ctaaacgtca ggcagtgacg     180
aacccgcaaa acactctgtt tgcgattaaa cgcctgattg gtcgccgctt ccaggacgaa     240
gaagtacagc gtgatgtttc catcatgccg ttcaaaatta ttgctgctga taacggcgac     300
gcatgggtcg aagttaaagg ccagaaaatg gcaccgccgc agatttctgc tgaagtgctg     360
aaaaaaatga agaaaaccgc tgaagattac ctgggtgaac ggtaactga agctgttatc     420 accgtaccgg catactttaa cgatgctcag cgtcaggcaa ccaaagacgc aggccgtatc     480
gctggtctgg aagtaaaacg tatcatcaac gaaccgaccg cagctgcgct ggcttacggt     540
ctggacaaag cactggcaa ccgtactatc gcggtttatg acctgggtgg tgtactttc     600 gatatttcta ttatcgaaat cgacgaagtt gacggcgaaa aaaccttcga agttctggca     660
accaacggtg atacccacct ggggggtgaa gacttcgaca gccgtctgat caactatctg     720
```

```
gttgaagaat tcaagaaaga tcagggcatt gacctgcgca acgatccgct ggcaatgcag    780
cgcctgaaag aagcggcaga aaagcgaaa atcgaactgt cttccgctca gcagaccgac    840
gttaacctgc catacatcac tgcagacgcg accggtccga acacatgaa catcaaagtg    900 actcgtgcga aactggaaag cctggttgaa gatctggtaa accgttccat tgagccgctg    960
aaagttgcac tgcaggacgc tggcctgtcc gtatctgata tcgacgacgt tatcctcgtt   1020
ggtggtcaga ctcgtatgcc aatggttcag aagaaagttg ctgagttctt tggtaaagag   1080
ccgcgtaaag acgttaaccc ggacgaagct gtagcaatcg gtgctgctgt tcagggtggt   1140
gttctgactg gtgacgtaaa agacgtactg ctgctggacg ttaccccgct gtctctgggt   1200
atcgaaacca tgggcggtgt gatgacgacg ctgatcgcga aaacaccac tatcccgacc   1260 aagcacagcc aggtgttctc taccgctgaa gacaaccagt ctgcggtaac catccatgtg   1320
ctgcagggtg aacgtaaacg tgcggctgat aacaaatctc tgggtcagtt caacctagat   1380
ggtatcaacc cggcaccgcg cggcatgccg cagatcgaag ttaccttcga tatcgatgct   1440
gacggtatcc tgcacgtttc cgcgaaagat aaaaacagcg gtaaagagca agatcacc   1500 atcaaggctt cttctggtct gaacgaagat gaaatccaga aatggtacg cgacgcagaa   1560 gctaacgccg aagctgaccg taagtttgaa gagctggtac agactcgcaa ccagggcgac   1620
catctgctgc acagcacccg taagcaggtt gaagaagcag cgacaaaact gccggctgac   1680
gacaaaactg ctatcgagtc tgcgctgact gcactggaaa ctgctctgaa aggtgaagac   1740
aaagccgcta tcgaagcgaa aatgcaggaa ctggcacagg tttcccagaa actgatggaa   1800
atcgcccagc agcaacatgc ccagcagcag actgccggtg ctgatgcttc tgcaaacaac   1860
gcgaaagatg acgatgttgt cgacgctgaa tttgaagaag tcaaagacaa aaaataa     1917
```

```
<210> SEQ ID NO 15
<211> LENGTH: 346
<212> TYPE: PRT
<213> ORGANISM: Escherichia coli

<400> SEQUENCE: 15

Met Lys Lys Thr Ala Ile Ala Ile Ala Val Ala Leu Ala Gly Phe Ala
  1               5                  10                  15

Thr Val Ala Gln Ala Ala Pro Lys Asp Asn Thr Trp Tyr Thr Gly Ala
                 20                  25                  30

Lys Leu Gly Trp Ser Gln Tyr His Asp Thr Gly Phe Ile Asn Asn Asn
             35                  40                  45

Gly Pro Thr His Glu Asn Gln Leu Gly Ala Gly Ala Phe Gly Gly Tyr
         50                  55                  60

Gln Val Asn Pro Tyr Val Gly Phe Glu Met Gly Tyr Asp Trp Leu Gly
 65                  70                  75                  80

Arg Met Pro Tyr Lys Gly Ser Val Glu Asn Gly Ala Tyr Lys Ala Gln
                 85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
    130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175
```

```
Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
        195                 200                 205

Glu Val Gln Thr Lys His Phe Thr Leu Lys Ser Asp Val Leu Phe Asn
    210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
                340                 345

<210> SEQ ID NO 16
<211> LENGTH: 1041
<212> TYPE: DNA
<213> ORGANISM: Escherichia coli

<400> SEQUENCE: 16
atgaaaaaga cagctatcgc gattgcagtg gcactggctg gtttcgctac cgtagcgcag        60
gccgctccga agataacac ctggtacact ggtgctaaac tgggctggtc ccagtaccat       120
gacactggtt tcatcaacaa caatggcccg accatgaaa accaactggg cgctggtgct       180
tttggtggtt accaggttaa cccgtatgtt ggctttgaaa tgggttacga ctggttaggt       240
cgtatgccgt acaaaggcag cgttgaaaac ggtgcataca agctcagggg cgttcaactg       300
accgctaaac tgggttaccc aatcactgac gacctggaca tctacactcg tctgggtggc       360
atggtatggc gtgcagacac taaatccaac gtttatggta aaaccacgga caccggcgtt       420
tctccggtct tcgctggcgg tgttgagtac gcgatcactc tgaaaatcgc tacccgtctg       480
gaataccagt ggaccaacaa catcggtgac gcacacacca tcggcactcg tccggacaac       540
ggcatgctga gctgggtgt ttcctaccgt ttcggtcagg gcgaagcagc tccagtagtt       600
gctccggctc cagctccggc accggaagta cagaccaagc acttcactct gaagtctgac       660
gttctgttca cttcaacaa agcaaccctg aaaccggaag tcaggctgc tctggatcag       720 ctgtacagcc agctgagcaa cctggatccg aaagacggtt ccgtagttgt tctgggttac       780
accgaccgca tcggttctga cgcttacaac cagggtctgt ccgagcgccg tgctcagtct       840
gttgttgatt acctgatctc caaaggtatc ccggcagaca agatctccgc acgtggtatg       900
ggcgaatcca acccggttac tggcaacacc tgtgacaacg tgaaacagcg tgctgcactg       960
atcgactgcc tggctccgga tcgtcgcgta gagatcgaag ttaaaggtat caaagacgtt      1020
gtaactcagc cgcaggctta a                                                1041

<210> SEQ ID NO 17
```

<211> LENGTH: 367
<212> TYPE: PRT
<213> ORGANISM: Escherichia coli

<400> SEQUENCE: 17

```
Met Lys Val Lys Val Leu Ser Leu Leu Val Pro Ala Leu Leu Val Ala
 1               5                  10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
                325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
        355                 360                 365
```

<210> SEQ ID NO 18
<211> LENGTH: 1104
<212> TYPE: DNA
<213> ORGANISM: Escherichia coli

<400> SEQUENCE: 18

```
atgaaagtta aagtactgtc cctcctggtc ccagctctgc tggtagcagg cgcagcaaac      60
gctgctgaag tttacaacaa agacggcaac aaattagatc tgtacggtaa agtagacggc     120
ctgcactatt tctctgacaa caaagatgta gatggcgacc agacctacat gcgtcttggc     180
ttcaaaggtg aaactcaggt tactgaccag ctgaccggtt acggccagtg gaatatcag      240
atccagggca cagcgctga aaacgaaaac aactcctgga cccgtgtggc attcgcaggt     300
ctgaaattcc aggatgtggg ttcttcgac tacggtcgta actacggcgt tgtttatgac     360
gtaacttcct ggaccgacgt actgccagaa ttcggtggtg cacctacgg ttctgacaac     420
ttcatgcagc agcgtggtaa cggcttcgcg acctaccgta acactgactt cttcggtctg     480
gttgacggcc tgaactttgc tgttcagtac cagggtaaaa acggcaaccc atctggtgaa     540
ggctttacta gtggcgtaac taacaacggt cgtgacgcac tgcgtcaaaa cggcgacggc     600
gtcggcggtt ctatcactta tgattacgaa ggtttcggta tcggtggtgc gatctccagc     660
tccaaacgta ctgatgctca gaacaccgct gcttacatcg gtaacggcga ccgtgctgaa     720
acctacactg tggtctgaa atacgacgct aacaacatct acctggctgc tcagtacacc     780
cagacctaca acgcaactcg cgtaggttcc ctgggttggg cgaacaaagc acagaacttc     840
gaagctgttg ctcagtacca gttcgacttc ggtctgcgtc cgtccctggc ttacctgcag     900
tctaaaggta aaacctgggt cgtggctac gacgacgaag atatcctgaa atatgttgat     960
gttggtgcta cctactactt caacaaaaac atgtccacct acgttgacta caaaatcaac    1020
ctgctggacg acaaccagtt cactcgtgac gctggcatca cactgataa catcgtagct    1080
ctgggtctgg tttaccagtt ctaa                                            1104
```

<210> SEQ ID NO 19
<211> LENGTH: 161
<212> TYPE: PRT
<213> ORGANISM: Escherichia coli

<400> SEQUENCE: 19

```
Met Lys Lys Trp Leu Leu Ala Ala Gly Leu Gly Leu Ala Leu Ala Thr
  1               5                  10                  15

Ser Ala Gln Ala Ala Asp Lys Ile Ala Ile Val Asn Met Gly Ser Leu
             20                  25                  30

Phe Gln Gln Val Ala Gln Lys Thr Gly Val Ser Asn Thr Leu Glu Asn
         35                  40                  45

Glu Phe Lys Gly Arg Ala Ser Glu Leu Gln Arg Met Glu Thr Asp Leu
     50                  55                  60

Gln Ala Lys Met Lys Lys Leu Gln Ser Met Lys Ala Gly Ser Asp Arg
 65                  70                  75                  80

Thr Lys Leu Glu Lys Asp Val Met Ala Gln Arg Gln Thr Phe Ala Gln
                 85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys
```

<210> SEQ ID NO 20
<211> LENGTH: 486
<212> TYPE: DNA
<213> ORGANISM: Escherichia coli

<400> SEQUENCE: 20

```
gtgaaaaagt ggttattagc tgcaggtctc ggtttagcac tggcaacttc tgctcaggcg      60
gctgacaaaa ttgcaatcgt caacatgggc agcctgttcc agcaggtagc gcagaaaacc     120
ggtgtttcta acacgctgga aaatgagttc aaaggccgtg ccagcgaact gcagcgtatg     180
gaaaccgatc tgcaggctaa atgaaaaag ctgcagtcca tgaaagcggg cagcgatcgc      240
actaagctgg aaaagacgt gatggctcag cgccagactt ttgctcagaa agcgcaggct      300
tttgagcagg atcgcgcacg tcgttccaac gaagaacgcg gcaaactggt tactcgtatc     360
cagactgctg tgaaatccgt tgccaacagc aggatatcg atctggttgt tgatgcaaac     420
gccgttgctt acaacagcag cgatgtaaaa gacatcactg ccgacgtact gaaacaggtt     480
aaataa                                                                486
```

<210> SEQ ID NO 21
<211> LENGTH: 130
<212> TYPE: PRT
<213> ORGANISM: Escherichia coli

<400> SEQUENCE: 21

```
Met Lys Lys Phe Ala Ala Val Ile Ala Val Met Ala Leu Cys Ser Ala
  1               5                  10                  15

Pro Val Met Ala Ala Glu Gln Gly Gly Phe Ser Gly Pro Ser Ala Thr
             20                  25                  30

Gln Ser Gln Ala Gly Gly Phe Gln Gly Pro Asn Gly Ser Val Thr Thr
         35                  40                  45

Val Glu Ser Ala Lys Ser Leu Arg Asp Asp Thr Trp Val Thr Leu Arg
     50                  55                  60

Gly Asn Ile Val Glu Arg Ile Ser Asp Asp Leu Tyr Val Phe Lys Asp
 65                  70                  75                  80

Ala Ser Gly Thr Ile Asn Val Asp Ile Asp His Lys Arg Trp Asn Gly
                 85                  90                  95

Val Thr Val Thr Pro Lys Asp Thr Val Glu Ile Gln Gly Glu Val Asp
            100                 105                 110

Lys Asp Trp Asn Ser Val Glu Ile Asp Val Lys Gln Ile Arg Lys Val
        115                 120                 125

Asn Pro
    130
```

<210> SEQ ID NO 22
<211> LENGTH: 393
<212> TYPE: DNA
<213> ORGANISM: Escherichia coli

<400> SEQUENCE: 22

```
atgaaaaaat tcgcagcagt aatcgcagta atggccctgt gcagcgcacc ggtgatggca      60
gcagagcagg gcggtttttc tggcccatcg gcaacgcaaa gtcaggccgg aggattccag     120
gggccgaacg gcagcgtaac gactgtagaa agcgcaaaat ccctgcgtga cgacacctgg     180
gtaaccctgc gcggcaatat cgttgaacga atctctgacg atctctacgt gttcaaagat     240
gccagcggta ctatcaatgt tgatatcgac cacaaacgct ggaacggcgt gacggtgacg     300
```

```
ccgaaagata cggttgagat tcagggtgaa gtcgataaag actggaattc tgttgaaatt    360
gacgtcaaac agatccgcaa agtaaatccg taa                                 393
```

<210> SEQ ID NO 23
<211> LENGTH: 151
<212> TYPE: PRT
<213> ORGANISM: Escherichia coli

<400> SEQUENCE: 23

```
Met Gln Glu Gly Gln Asn Arg Lys Thr Ser Ser Leu Ser Ile Leu Ala
1               5                   10                  15

Ile Ala Gly Val Glu Pro Tyr Gln Glu Lys Pro Gly Glu Glu Tyr Met
            20                  25                  30

Asn Glu Ala Gln Leu Ala His Phe Arg Arg Ile Leu Glu Ala Trp Arg
        35                  40                  45

Asn Gln Leu Arg Asp Glu Val Asp Arg Thr Val Thr His Met Gln Asp
    50                  55                  60

Glu Ala Ala Asn Phe Pro Asp Pro Val Asp Arg Ala Ala Gln Glu Glu
65                  70                  75                  80

Glu Phe Ser Leu Glu Leu Arg Asn Arg Asp Arg Glu Arg Lys Leu Ile
                85                  90                  95

Lys Lys Ile Glu Lys Thr Leu Lys Lys Val Glu Asp Glu Asp Phe Gly
            100                 105                 110

Tyr Cys Glu Ser Cys Gly Val Glu Ile Gly Ile Arg Arg Leu Glu Ala
        115                 120                 125

Arg Pro Thr Ala Asp Leu Cys Ile Asp Cys Lys Thr Leu Ala Glu Ile
    130                 135                 140

Arg Glu Lys Gln Met Ala Gly
145                 150
```

<210> SEQ ID NO 24
<211> LENGTH: 456
<212> TYPE: DNA
<213> ORGANISM: Escherichia coli

<400> SEQUENCE: 24

```
atgcaagaag gcaaaaccg taaaacatcg tccctgagta ttctcgccat cgctggggtg     60
gaaccatatc aggagaagcc gggcgaagag tatatgaatg aagcccagct ggcgcacttc    120
cgtcgtattc tggaagcatg gcgtaatcaa ctcaggatg aagtcgatcg caccgttaca     180
catatgcagg atgaagcagc caacttcccg gacccggtag accgtgcagc caggaagaa     240 gagttcagcc tcgaactgcg taaccgcgat cgcgagcgta agctgatcaa aaagatcgag    300
aagacgctga aaaagtgga gacgaagat tccggctact gcgaatcctg cggtgttgaa      360
attggtattc gccgtctgga agcgcgcccg acagccgatc tgtgcatcga ctgcaaaacg    420
ctggctgaaa ttcgcgaaaa acagatggct ggctaa                             456
```

<210> SEQ ID NO 25
<211> LENGTH: 137
<212> TYPE: PRT
<213> ORGANISM: Escherichia coli

<400> SEQUENCE: 25

```
Met Ser Glu Ala Leu Lys Ile Leu Asn Asn Ile Arg Thr Leu Arg Ala
1               5                   10                  15

Gln Ala Arg Glu Cys Thr Leu Glu Thr Leu Glu Glu Met Leu Glu Lys
            20                  25                  30
```

```
Leu Glu Val Val Asn Glu Arg Arg Glu Glu Ser Ala Ala Ala
         35                  40                  45
Ala Glu Val Glu Glu Arg Thr Arg Lys Leu Gln Gln Tyr Arg Glu Met
 50                  55                  60
Leu Ile Ala Asp Gly Ile Asp Pro Asn Glu Leu Leu Asn Ser Leu Ala
 65                  70                  75                  80
Ala Val Lys Ser Gly Thr Lys Ala Lys Arg Ala Gln Arg Pro Ala Lys
                 85                  90                  95
Tyr Ser Tyr Val Asp Glu Asn Gly Thr Lys Thr Trp Thr Gly Gln
                100                 105                 110
Gly Arg Thr Pro Ala Val Ile Lys Lys Ala Met Asp Glu Gln Gly Lys
                115                 120                 125
Ser Leu Asp Asp Phe Leu Ile Lys Gln
                130                 135

<210> SEQ ID NO 26
<211> LENGTH: 414
<212> TYPE: DNA
<213> ORGANISM: Escherichia coli

<400> SEQUENCE: 26
atgagcgaag cacttaaaat tctgaacaac atccgtactc ttcgtgcgca ggcaagagaa      60
tgtacacttg aaacgctgga agaaatgctg gaaaaattag aagttgttgt taacgaacgt    120
cgcgaagaag aaagcgcggc tgctgctgaa gttgaagagc gcactcgtaa actgcagcaa    180
tatcgcgaaa tgctgatcgc tgacggtatt gacccgaacg aactgctgaa tagccttgct    240
gccgttaaat ctggcaccaa agctaaacgt gctcagcgtc cggcaaaata tagctacgtt    300
gacgaaaacg gcgaaactaa aacctggact ggccaaggcc gtactccagc tgtaatcaaa    360
aaagcaatgg atgagcaagg taatccctc gacgatttcc tgatcaagca ataa           414

<210> SEQ ID NO 27
<211> LENGTH: 70
<212> TYPE: PRT
<213> ORGANISM: Pseudomonas putida

<400> SEQUENCE: 27

Met Ser Asn Arg Gln Gln Gly Thr Val Lys Trp Phe Asn Asp Glu Lys
  1               5                  10                  15
Gly Tyr Gly Phe Ile Thr Pro Ala Gly Gly Asp Asp Leu Phe Val
                 20                  25                  30
His Phe Lys Ala Ile Glu Ser Asp Gly Phe Lys Ser Leu Lys Glu Gly
                 35                  40                  45
Gln Thr Val Ser Phe Val Ala Glu Arg Gly Gln Lys Gly Met Gln Ala
 50                  55                  60
Ala Gln Val Arg Pro Glu
 65                  70

<210> SEQ ID NO 28
<211> LENGTH: 213
<212> TYPE: DNA
<213> ORGANISM: Pseudomonas putida

<400> SEQUENCE: 28
atgtccaatc gccaacaagg caccgtcaaa tggttcaatg atgagaaagg ctacggcttc      60
atcaccccag caggcggcgg cgacgacctg ttcgtacact tcaaagccat cgaatctgac    120
ggcttcaaga gcctgaaaga aggccagact gtttccttcg tcgccgagcg cggccagaag    180
```

```
ggcatgcagg ctgcacaggt tcgtccggag taa                              213
```

<210> SEQ ID NO 29
<211> LENGTH: 425
<212> TYPE: PRT
<213> ORGANISM: Corynebacterium glutamicum

<400> SEQUENCE: 29

```
Met Ala Glu Ile Met His Val Phe Ala Arg Glu Ile Leu Asp Ser Arg
 1               5                  10                  15

Gly Asn Pro Thr Val Glu Ala Glu Val Phe Leu Asp Asp Gly Ser His
                20                  25                  30

Gly Val Ala Gly Val Pro Ser Gly Ala Ser Thr Gly Val His Glu Ala
            35                  40                  45

His Glu Leu Arg Asp Gly Asp Arg Tyr Leu Gly Lys Gly Val Leu
    50                  55                  60

Lys Ala Val Glu Asn Val Asn Glu Glu Ile Gly Asp Glu Leu Ala Gly
 65                  70                  75                  80

Leu Glu Ala Asp Asp Gln Arg Leu Ile Asp Glu Ala Met Ile Lys Leu
                85                  90                  95

Asp Gly Thr Ala Asn Lys Ser Arg Leu Gly Ala Asn Ala Ile Leu Gly
                100                 105                 110

Val Ser Met Ala Val Ala Lys Ala Ala Ala Asp Ser Ala Gly Leu Pro
            115                 120                 125

Leu Phe Arg Tyr Ile Gly Gly Pro Asn Ala His Val Leu Pro Val Pro
    130                 135                 140

Met Met Asn Ile Ile Asn Gly Gly Ala His Ala Asp Ser Gly Val Asp
145                 150                 155                 160

Val Gln Glu Phe Met Ile Ala Pro Ile Gly Ala Glu Thr Phe Ser Glu
                165                 170                 175

Ala Leu Arg Asn Gly Ala Glu Val Tyr His Ala Leu Lys Ser Val Ile
                180                 185                 190

Lys Glu Lys Gly Leu Ser Thr Gly Leu Gly Asp Glu Gly Gly Phe Ala
            195                 200                 205

Pro Ser Val Gly Ser Thr Arg Glu Ala Leu Asp Leu Ile Val Glu Ala
    210                 215                 220

Ile Glu Lys Ala Gly Phe Thr Pro Gly Lys Asp Ile Ala Leu Ala Leu
225                 230                 235                 240

Asp Val Ala Ser Ser Glu Phe Phe Lys Asp Gly Thr Tyr His Phe Glu
                245                 250                 255

Gly Gly Gln His Ser Ala Ala Glu Met Ala Asn Val Tyr Ala Glu Leu
            260                 265                 270

Val Asp Ala Tyr Pro Ile Val Ser Ile Glu Asp Pro Leu Gln Glu Asp
    275                 280                 285

Asp Trp Glu Gly Tyr Thr Asn Leu Thr Ala Thr Ile Gly Asp Lys Val
290                 295                 300

Gln Ile Val Gly Asp Asp Phe Phe Val Thr Asn Pro Glu Arg Leu Lys
305                 310                 315                 320

Glu Gly Ile Ala Lys Lys Ala Ala Asn Ser Ile Leu Val Lys Val Asn
                325                 330                 335

Gln Ile Gly Thr Leu Thr Glu Thr Phe Asp Ala Val Asp Met Ala His
            340                 345                 350

Arg Ala Gly Tyr Thr Ser Met Met Ser His Arg Ser Gly Glu Thr Glu
    355                 360                 365

Asp Thr Thr Ile Ala Asp Leu Ala Val Ala Leu Asn Cys Gly Gln Ile
```

```
          370              375             380
Lys Thr Gly Ala Pro Ala Arg Ser Asp Arg Val Ala Lys Tyr Asn Gln
385                 390             395                 400

Leu Leu Arg Ile Glu Gln Leu Leu Gly Asp Ala Gly Val Tyr Ala Gly
                405             410                 415

Arg Ser Ala Phe Pro Arg Phe Gln Gly
            420             425
```

<210> SEQ ID NO 30
<211> LENGTH: 1278
<212> TYPE: DNA
<213> ORGANISM: Corynebacterium glutamicum

<400> SEQUENCE: 30

| | | | | | |
|---|---|---|---|---|---|
| gtggctgaaa | tcatgcacgt | attcgctcgc | gaaattctcg | actcccgcgg | taacccaacc | 60 |
| gtcgaggcag | aggttttcct | ggatgacggt | tcccacggtg | tcgcaggtgt | tccatccggc | 120 |
| gcatccaccg | gcgtccacga | ggctcatgag | ctgcgtgacg | gtggcgatcg | ctacctgggc | 180 |
| aagggcgttt | tgaaggcagt | tgaaaacgtc | aacgaagaaa | tcggcgacga | gctcgctggc | 240 |
| ctagaggctg | acgatcagcg | cctcatcgac | gaagcaatga | tcaagcttga | tggcaccgcc | 300 |
| aacaagtccc | gcctgggtgc | aaacgcaatc | cttggtgttt | ccatggctgt | tgcaaaggct | 360 |
| gctgctgatt | ccgcaggcct | cccactgttc | cgctacatcg | gtggaccaaa | cgcacacgtt | 420 |
| cttccagttc | caatgatgaa | catcatcaac | ggtggcgctc | acgctgactc | cggtgttgac | 480 |
| gttcaggaat | tcatgatcgc | tccaatcggt | gcagagacct | ctctgaggc | tctccgcaac | 540 |
| ggcgcggagg | tctaccacgc | actgaagtcc | gtcatcaagg | aaaagggcct | gtccaccgga | 600 |
| cttggcgatg | agggcggctt | cgctccttcc | gtcggctcca | cccgtgaggc | tcttgacctt | 660 |
| atcgttgagg | caatcgagaa | ggctggcttc | accccaggca | aggacatcgc | tcttgctctg | 720 |
| gacgttgctt | cctctgagtt | cttcaaggac | ggcacctacc | acttcgaagg | tggccagcac | 780 |
| tccgcagctg | agatggcaaa | cgtttacgct | gagctcgttg | acgcgtaccc | aatcgtctcc | 840 |
| atcgaggacc | cactgcagga | agatgactgg | gagggttaca | ccaacctcac | cgcaaccatc | 900 |
| ggcgacaagg | ttcagatcgt | tggcgacgac | ttcttcgtca | ccaaccctga | gcgcctgaag | 960 |
| gagggcatcg | ctaagaaggc | tgccaactcc | atcctggtta | aggtgaacca | gatcggtacc | 1020 |
| ctcaccgaga | ccttcgacgc | tgtcgacatg | gctcaccgcg | caggctacac | ctccatgatg | 1080 |
| tcccaccgtt | ccggtgagac | cgaggacacc | accattgctg | acctcgcagt | tgcactcaac | 1140 |
| tgtggccaga | tcaagactgg | tgctccagca | cgttccgacc | gtgtcgcaaa | gtacaaccag | 1200 |
| cttctccgca | tcgagcagct | gcttggcgac | gccggcgtct | acgcaggtcg | cagcgcattc | 1260 |
| ccacgctttc | agggctaa | | | | | 1278 |

<210> SEQ ID NO 31
<211> LENGTH: 471
<212> TYPE: PRT
<213> ORGANISM: Escherichia coli

<400> SEQUENCE: 31

```
Met Lys Gln Ser Thr Ile Ala Leu Ala Leu Leu Pro Leu Leu Phe Thr
 1               5                  10                  15

Pro Val Thr Lys Ala Arg Thr Pro Glu Met Pro Val Leu Glu Asn Arg
                20                  25                  30

Ala Ala Gln Gly Asp Ile Thr Ala Pro Gly Gly Ala Arg Arg Leu Thr
            35                  40                  45
```

```
Gly Asp Gln Thr Ala Ala Leu Arg Asp Ser Leu Ser Asp Lys Pro Ala
 50                  55                  60
Lys Asn Ile Ile Leu Ile Gly Asp Gly Met Gly Asp Ser Glu Ile
 65                  70                  75                  80
Thr Ala Ala Arg Asn Tyr Ala Glu Gly Ala Gly Gly Phe Phe Lys Gly
                     85                  90                  95
Ile Asp Ala Leu Pro Leu Thr Gly Gln Tyr Thr His Tyr Ala Leu Asn
                100                 105                 110
Lys Lys Thr Gly Lys Pro Asp Tyr Val Thr Asp Ser Ala Ala Ser Ala
                115                 120                 125
Thr Ala Trp Ser Thr Gly Val Lys Thr Tyr Asn Gly Ala Leu Gly Val
            130                 135                 140
Asp Ile His Glu Lys Asp His Pro Thr Ile Leu Glu Met Ala Lys Ala
145                 150                 155                 160
Ala Gly Leu Ala Thr Gly Asn Val Ser Thr Ala Glu Leu Gln Asp Ala
                165                 170                 175
Thr Pro Ala Ala Leu Val Ala His Val Thr Ser Arg Lys Cys Tyr Gly
                180                 185                 190
Pro Ser Ala Thr Ser Glu Lys Cys Pro Gly Asn Ala Leu Glu Lys Gly
            195                 200                 205
Gly Lys Gly Ser Ile Thr Glu Gln Leu Leu Asn Ala Arg Ala Asp Val
            210                 215                 220
Thr Leu Gly Gly Gly Ala Lys Thr Phe Ala Glu Thr Ala Thr Ala Gly
225                 230                 235                 240
Glu Trp Gln Gly Lys Thr Leu Arg Glu Gln Ala Gln Ala Arg Gly Tyr
                245                 250                 255
Gln Leu Val Ser Asp Ala Ala Ser Leu Asn Ser Val Thr Glu Ala Asn
            260                 265                 270
Gln Gln Lys Pro Leu Leu Gly Leu Phe Ala Asp Gly Asn Met Pro Val
            275                 280                 285
Arg Trp Leu Gly Pro Lys Ala Thr Tyr His Gly Asn Ile Asp Lys Pro
            290                 295                 300
Ala Val Thr Cys Thr Pro Asn Pro Gln Arg Asn Asp Ser Val Pro Thr
305                 310                 315                 320
Leu Ala Gln Met Thr Asp Lys Ala Ile Glu Leu Leu Ser Lys Asn Glu
                325                 330                 335
Lys Gly Phe Phe Leu Gln Val Glu Gly Ala Ser Ile Asp Lys Gln Asp
                340                 345                 350
His Ala Ala Asn Pro Cys Gly Gln Ile Gly Glu Thr Val Asp Leu Asp
            355                 360                 365
Glu Ala Val Gln Arg Ala Leu Glu Phe Ala Lys Lys Glu Gly Asn Thr
370                 375                 380
Leu Val Ile Val Thr Ala Asp His Ala His Ala Ser Gln Ile Val Ala
385                 390                 395                 400
Pro Asp Thr Lys Ala Pro Gly Leu Thr Gln Ala Leu Asn Thr Lys Asp
                405                 410                 415
Gly Ala Val Met Val Met Ser Tyr Gly Asn Ser Glu Glu Asp Ser Gln
                420                 425                 430
Glu His Thr Gly Ser Gln Leu Arg Ile Ala Ala Tyr Gly Pro His Ala
            435                 440                 445
Ala Asn Val Val Gly Leu Thr Asp Gln Thr Asp Leu Phe Tyr Thr Met
            450                 455                 460
Lys Ala Ala Leu Gly Leu Lys
465                 470
```

<210> SEQ ID NO 32
<211> LENGTH: 1416
<212> TYPE: DNA
<213> ORGANISM: Escherichia coli

<400> SEQUENCE: 32

```
gtgaaacaaa gcactattgc actggcactc ttaccgttac tgtttacccc tgtgacaaaa      60
gcccggacac cagaaatgcc tgttctggaa accgggctg ctcagggcga tattactgca     120
cccggcggtg ctcgccgttt aacgggtgat cagactgccg ctctgcgtga ttctcttagc    180
gataaacctg caaaaaatat tattttgctg attggcgatg ggatggggga ctcggaaatt    240
actgccgcac gtaattatgc cgaaggtgcg ggcggctttt ttaaaggtat agatgcctta    300
ccgcttaccg ggcaatacac tcactatgcg ctgaataaaa aaaccggcaa accggactac    360
gtcaccgact cggctgcatc agcaaccgcc tggtcaaccg tgtcaaaac ctataacggc     420
gcgctgggcg tcgatattca cgaaaaagat cacccaacga ttctggaaat ggcaaaagcc    480
gcaggtctgg cgaccggtaa cgtttctacc gcagagttgc aggatgccac gcccgctgcg    540
ctggtggcac atgtgacctc gcgcaaatgc tacggtccga gcgcgaccag tgaaaaatgt    600
ccgggtaacg ctctggaaaa aggcggaaaa ggatcgatta ccgaacagct gcttaacgct    660
cgtgccgacg ttacgcttgg cggcggcgca aaaacctttg ctgaaacggc aaccgctggt    720
gaatggcagg gaaaaacgct gcgtgaacag gcacaggcgc gtggttatca gttggtgagc    780
gatgctgcct cactgaattc ggtgacggaa gcgaatcagc aaaaacccct gcttggcctg    840
tttgctgacg gcaatatgcc agtgcgctgg ctaggaccga agcaacgta ccatggcaat     900
atcgataagc ccgcagtcac ctgtacgcca aatccgcaac gtaatgacag tgtaccaacc    960
ctggcgcaga tgaccgacaa agccattgaa ttgttgagta aaaatgagaa aggcttttc    1020
ctgcaagttg aaggtgcgtc aatcgataaa caggatcatg ctgcgaatcc ttgtgggcaa   1080
attggcgaga cggtcgatct cgatgaagcc gtacaacggg cgctggaatt cgctaaaaag   1140
gagggtaaca cgctggtcat agtcaccgct gatcacgccc acgccagcca gattgttgcg   1200
ccggatacca aagctccggg cctcacccag cgctaaata ccaaagatgg cgcagtgatg    1260
gtgatgagtt acgggaactc cgaagaggat tcacaagaac ataccggcag tcagttgcgt   1320
attgcggcgt atggcccgca tgccgccaat gttgttggac tgaccgacca gaccgatctc   1380
ttctacacca tgaaagccgc tctggggctg aaataa                             1416
```

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33

```
atcgaattct gcgcaacacg atgaagctca ac                                    32
```

<210> SEQ ID NO 34
<211> LENGTH: 31
<212> TYPE: DNA
<213> ORGANISM: Artificial Sequence
<220> FEATURE:
<223> OTHER INFORMATION: Synthetic Construct

<400> SEQUENCE: 34

```
gttgagctcg tgttgttgtc ttcctctttt g                                     31
```

<210> SEQ ID NO 35
<211> LENGTH: 29
<212> TYPE: DNA
<213> ORGANISM: Artificial Sequence
<220> FEATURE:
<223> OTHER INFORMATION: Synthetic Construct

<400> SEQUENCE: 35
gttgtcgaca tggcagttgt taaatgtaa                                29

<210> SEQ ID NO 36
<211> LENGTH: 30
<212> TYPE: DNA
<213> ORGANISM: Artificial Sequence
<220> FEATURE:
<223> OTHER INFORMATION: Synthetic Construct

<400> SEQUENCE: 36
gttgcggccg ctttgctacg gcgacgtacg                               30

<210> SEQ ID NO 37
<211> LENGTH: 32
<212> TYPE: DNA
<213> ORGANISM: Artificial Sequence
<220> FEATURE:
<223> OTHER INFORMATION: Synthetic Construct

<400> SEQUENCE: 37
catcgaattc tatggcagtt gttaaatgta aa                            32

<210> SEQ ID NO 38
<211> LENGTH: 32
<212> TYPE: DNA
<213> ORGANISM: Artificial Sequence
<220> FEATURE:
<223> OTHER INFORMATION: Synthetic Construct

<400> SEQUENCE: 38
agttgagctc gttttgctac ggcgacgtac ga                            32

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
agtaatgcta gcgcagttgt taaatgtaaa ccg                           33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
acaatctcga gttactgctt gtggcc                                   26

<210> SEQ ID NO 41
<211> LENGTH: 375
<212> TYPE: PRT
<213> ORGANISM: Mus musculus

<400> SEQUENCE: 41

```
Met Glu Glu Glu Ile Ala Ala Leu Val Ile Asp Asn Gly Ser Gly Met
  1               5                  10                 15

Cys Lys Ala Gly Phe Ala Gly Asp Asp Ala Pro Arg Ala Val Phe Pro
             20                  25                  30

Ser Ile Val Gly Arg Pro Arg His Gln Gly Val Met Val Gly Met Gly
         35                  40                  45

Gln Lys Asp Ser Tyr Val Gly Asp Glu Ala Gln Ser Lys Arg Gly Ile
 50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
             85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
            115                 120                 125

Thr Pro Ala Met Tyr Val Ala Ile Gln Ala Val Leu Ser Leu Tyr Ala
            130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
                180                 185                 190

Leu Thr Glu Arg Gly Tyr Ser Phe Thr Thr Thr Ala Glu Arg Glu Ile
            195                 200                 205

Val Arg Asp Ile Lys Glu Lys Leu Cys Tyr Val Ala Leu Asp Phe Glu
210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
            275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
            370                 375

<210> SEQ ID NO 42
<211> LENGTH: 1128
<212> TYPE: DNA
<213> ORGANISM: Mus musculus

<400> SEQUENCE: 42
```

```
atggaagaag aaatcgccgc actcgtcatt gacaatggct ccggcatgtg caaagccggc    60
tttgctggcg acgacgcccc cagggccgtg ttcccttcca cgtagggcg ccccgacac    120
cagggcgtca tggtgggcat gggccagaaa gactcatacg tgggtgacga ggcccagagc   180
aagagggta tcctgaccct gaagtaccct atcgaacacg gcattgtcac taactgggac   240
gacatggaga gatctggca ccacaccttc tacaatgagc tgcgtgtggc tcctgaggag   300
cacccggtgc ttctgaccga ggccccctg aaccccaaag ctaacagaga gaagatgacg    360
cagataatgt ttgaaaccttt caataccccca gccatgtacg tggccattca ggcggtgctg    420
tccttgtatg catctgggcg caccactggc attgtcatgg actctggtga cggggtcaca    480
cacacagtgc ccatctatga gggctacgcc cttccccacg ccatcttgcg tctggacctg    540
gctggccggg acctgacaga ctacctcatg aagatcctga ctgaacgggg ctacagcttt    600
accaccactg ctgagaggga aattgttcgt gacataaagg agaagctgtg ctatgttgcc    660
ctggattttg agcaagaaat ggctactgct gcatcatctt cctccttgga gaagagttac    720
gagctgcccg acgggcaggt gatcaccatt ggcaatgagc ggttccggtg tccggaggca    780
ctcttccagc cttccttcct gggcatggag tcctgtggta tccatgagac cactttcaac    840
tccatcatga agtgtgatgt ggatatccgc aaagacctgt atgccaatac agtgctgtct    900
ggtggtacca ccatgtaccc aggcattgct gacaggatgc agaaggagat cacagcccta    960
gcacctagca cgatgaagat taagatcatt gctcccctg agcgcaagta ctcagtctgg   1020
atcggtggct ccattctggc ctcactgtcc accttccagc agatgtggat cagcaagcag   1080
gagtatgatg agtcaggccc ctccatcgtc caccgcaaat gcttctag                1128

<210> SEQ ID NO 43
<211> LENGTH: 375
<212> TYPE: PRT
<213> ORGANISM: Mus musculus

<400> SEQUENCE: 43

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175
```

```
Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
370                 375

<210> SEQ ID NO 44
<211> LENGTH: 1128
<212> TYPE: DNA
<213> ORGANISM: Mus musculus

<400> SEQUENCE: 44
atggatgacg atatcgctgc gctggtcgtc gacaacggct ccggcatgtg caaagccggc      60
ttcgcgggcg acgatgctcc ccgggctgta ttcccctcca tcgtgggccg ccctaggcac     120
cagggtgtga tggtgggaat gggtcagaag gactcctatg tgggtgacga ggcccagagc     180
aagagaggta tcctgaccct gaagtacccc attaacatgg cattgttac caactgggac     240 gacatggaga gatctggca ccacaccttc tacaatgagc tgcgtgtggc ccctgaggag     300 cacctgtgc tgctcaccga gccccctg aaccctaagg ccaaccgtga aaagatgacc     360
cagatcatgt ttgagacctt caacacccca gccatgtacg tagccatcca ggctgtgctg     420
tccctgtatg cctctggtcg taccacaggc attgtgatgg actccggaga cggggtcacc     480
cacactgtgc ccatctacga gggctatgct ctccctcacg ccatcctgcg tctggacctg     540
gctggccggg acctgacaga ctacctcatg aagatcctga ccgagcgtgg ctacagcttc     600
accaccacag ctgagaggga aatcgtgcgt gacatcaaag agaagctgtg ctatgttgct     660
ctagacttcg agcaggagat ggccactgcc gcatcctctt cctccctgga aagagctat     720 gagctgcctg acggccaggt catcactatt ggcaacgagc ggttccgatg ccctgaggct     780
cttttccagc cttccttctt gggtatggaa tcctgtggca tccatgaaac acattcaat     840 tccatcatga gtgtgacgt tgacatccgt aaagacctct atgccaacac agtgctgtct     900
ggtggtacca ccatgtaccc aggcattgct gacaggatgc agaaggagat tactgctctg     960
gctcctagca ccatgaagat caagatcatt gctcctcctg agcgcaagta ctctgtgtgg    1020
```
atcggtggct ccatcctggc ctcactgtcc accttccagc agatgtggat cagcaagcag   1080
gagtacgatg agtccggccc ctccatcgtg caccgcaagt gcttctag              1128

<210> SEQ ID NO 45
<211> LENGTH: 60
<212> TYPE: PRT
<213> ORGANISM: Artificial Sequence
<220> FEATURE:
<223> OTHER INFORMATION: Synthetic Construct

<400> SEQUENCE: 45

Met Ala Val Val Lys Cys Lys Pro Thr Ser Pro Gly Arg Arg His Val
 1               5                  10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly Gly His Lys Gln
    50                  55                  60

<210> SEQ ID NO 46
<211> LENGTH: 180
<212> TYPE: DNA
<213> ORGANISM: Artificial Sequence
<220> FEATURE:
<223> OTHER INFORMATION: Synthetic Construct

<400> SEQUENCE: 46
atggcagttg ttaaatgtaa accgacatct ccgggtcgtc gccacgtagt taaagtggtt   60
aaccctgagc tgcacaaggg caaaccttt gctccgttgc tggaaaaaaa cagcaaatcc   120
ggtggtcgta acaacaatgg ccgtatcacc actcgtcata tcggtggtgg ccacaagcag   180

<210> SEQ ID NO 47
<211> LENGTH: 70
<212> TYPE: PRT
<213> ORGANISM: Artificial Sequence
<220> FEATURE:
<223> OTHER INFORMATION: Synthetic Construct

<400> SEQUENCE: 47

Val Leu Gly Lys Ala Gly Ala Ala Arg Trp Arg Gly Val Arg Pro Thr
 1               5                  10                  15

Val Arg Gly Thr Ala Met Asn Pro Val Asp His Pro His Gly Gly Gly
            20                  25                  30

Glu Gly Arg Asn Phe Gly Lys His Pro Val Thr Pro Trp Gly Val Gln
        35                  40                  45

Thr Lys Gly Lys Lys Thr Arg Ser Asn Lys Arg Thr Asp Lys Phe Ile
    50                  55                  60

Val Arg Arg Arg Ser Lys
65                  70

<210> SEQ ID NO 48
<211> LENGTH: 213
<212> TYPE: DNA
<213> ORGANISM: Artificial Sequence
<220> FEATURE:
<223> OTHER INFORMATION: Synthetic Construct

<400> SEQUENCE: 48
gttctgggta aagcaggtgc tgcacgctgg cgtggtgttc gtccgaccgt tcgcggtacc   60

```
gcgatgaacc cggtagacca cccacatggt ggtggtgaag gtcgtaactt tggtaagcac    120
ccggtaactc cgtggggcgt tcagaccaaa ggtaagaaga cccgcagcaa caagcgtact    180
gataaattca tcgtacgtcg ccgtagcaaa taa                                 213
```

<210> SEQ ID NO 49
<211> LENGTH: 130
<212> TYPE: PRT
<213> ORGANISM: Artificial Sequence
<220> FEATURE:
<223> OTHER INFORMATION: Synthetic Construct

<400> SEQUENCE: 49

```
Met Ala Val Val Lys Cys Lys Pro Thr Ser Pro Gly Arg Arg His Val
1               5                   10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly His Lys Gln Val Leu Gly Lys
    50                  55                  60

Ala Gly Ala Ala Arg Trp Arg Gly Val Arg Pro Thr Val Arg Gly Thr
65                  70                  75                  80

Ala Met Asn Pro Val Asp His Pro His Gly Gly Gly Glu Gly Arg Asn
                85                  90                  95

Phe Gly Lys His Pro Val Thr Pro Trp Gly Val Gln Thr Lys Gly Lys
            100                 105                 110

Lys Thr Arg Ser Asn Lys Arg Thr Asp Lys Phe Ile Val Arg Arg Arg
        115                 120                 125

Ser Lys
    130
```

<210> SEQ ID NO 50
<211> LENGTH: 393
<212> TYPE: DNA
<213> ORGANISM: Artificial Sequence
<220> FEATURE:
<223> OTHER INFORMATION: Synthetic Construct

<400> SEQUENCE: 50

```
atggcagttg ttaaatgtaa accgacatct ccgggtcgtc gccacgtagt taaagtggtt     60
aaccctgagc tgcacaaggg caaacctttt gctccgttgc tggaaaaaaa cagcaaatcc    120
ggtggtcgta acaacaatgg ccgtatcacc actcgtcata tcggtggtgg ccacaagcag    180
gttctgggta aagcaggtgc tgcacgctgg cgtggtgttc gtccgaccgt tcgcggtacc    240
gcgatgaacc cggtagacca cccacatggt ggtggtgaag gtcgtaactt tggtaagcac    300
ccggtaactc cgtggggcgt tcagaccaaa ggtaagaaga cccgcagcaa caagcgtact    360
gataaattca tcgtacgtcg ccgtagcaaa taa                                 393
```